(12) United States Patent
Wagner et al.

(10) Patent No.: US 10,266,656 B2
(45) Date of Patent: Apr. 23, 2019

(54) SILICONE COMPOUNDS AND COMPOSITIONS THEREOF FOR THE TREATMENT OF AMINO ACID BASED SUBSTRATES

(71) Applicant: Momentive Performance Materials GmbH, Leverkusen (DE)

(72) Inventors: Roland Wagner, Bonn (DE); Anne Dussaud, Tarrytown, NY (US); Karl-Heinz Stachulla, Leverkusen (DE); Christian Wenske, Solingen (DE); Katharina Streicher, Leverkusen (DE); Martin Moeller, Aachen (DE); Andrea Koerner, Herzogenrath (DE); Barbara Dittrich, Aachen (DE); Robin Heedfeld, Aachen (DE); Crisan Popescu, Frankfurt a.M. (DE); Helmut Keul, Aachen (DE); Xiaomin Zhu, Aachen (DE); Mériem Er-Rafik, Strasbourg (FR); Kunshan Sun, Millwood, NY (US)

(73) Assignee: Momentive Performance Materials GmbH, Leverkusen (DE)

(*) Notice: Subject to any disclaimer, the term of this patent is extended or adjusted under 35 U.S.C. 154(b) by 0 days.

(21) Appl. No.: 15/512,623

(22) PCT Filed: Sep. 22, 2015

(86) PCT No.: PCT/EP2015/071678
§ 371 (c)(1),
(2) Date: Mar. 20, 2017

(87) PCT Pub. No.: WO2016/046178
PCT Pub. Date: Mar. 31, 2016

(65) Prior Publication Data
US 2017/0291994 A1 Oct. 12, 2017

Related U.S. Application Data

(60) Provisional application No. 62/053,870, filed on Sep. 23, 2014.

(51) Int. Cl.
  *A61K 8/89* (2006.01)
  *A61Q 5/04* (2006.01)
  (Continued)

(52) U.S. Cl.
  CPC ............... *C08G 77/38* (2013.01); *A61K 8/89* (2013.01); *A61K 8/892* (2013.01); *A61K 8/898* (2013.01); *A61K 8/899* (2013.01); *A61Q 5/04* (2013.01); *A61Q 5/12* (2013.01); *C08G 77/388* (2013.01); *C08G 77/392* (2013.01); *C08L 83/08* (2013.01); *A61K 2800/94* (2013.01); *C08G 77/14* (2013.01); *C08G 77/26* (2013.01)

(58) Field of Classification Search
None
See application file for complete search history.

(56) References Cited

U.S. PATENT DOCUMENTS 2,032,624 A 3/1936 Lyons
2,770,631 A 11/1956 Merker
(Continued)

FOREIGN PATENT DOCUMENTS

| EP | 0295780 A1 | 12/1988 |
|---|---|---|
| GB | 722822 | 2/1955 |
| GB | 1182939 | 3/1970 |

OTHER PUBLICATIONS

International Search Report for corresponding PCT/EP2015/071678 dated Dec. 23, 2015, six pages.

*Primary Examiner* — Aradhana Sasan
(74) *Attorney, Agent, or Firm* — Rankin, Hill & Clark LLP

(57) ABSTRACT

Organofunctional polyorganosiloxanes, their use in cosmetic compositions, method for treating amino acid based substrates with organofunctional polyorganosiloxanes, compositions comprising the organofunctional polyorganosiloxanes useful for hair straightening and shaping as well as hair coloration and hair color retention.

23 Claims, 1 Drawing Sheet

Example of a stress-strain curve of treated (2) and untreated hair (1)

(51) Int. Cl.
*A61Q 5/12* (2006.01)
*A61K 8/892* (2006.01)
*A61K 8/898* (2006.01)
*A61K 8/899* (2006.01)
*C08G 77/14* (2006.01)
*C08G 77/26* (2006.01)
*C08G 77/38* (2006.01)
*C08L 83/08* (2006.01)
*C08G 77/388* (2006.01)
*C08G 77/392* (2006.01)

(56) References Cited

U.S. PATENT DOCUMENTS

| | | |
|---|---|---|
| 3,432,536 A | 3/1969 | Simoneau |
| 4,787,910 A | 11/1988 | Hendricks et al. |
| 5,679,619 A | 10/1997 | Morgan et al. |
| 5,747,016 A | 5/1998 | Yui et al. |
| 5,935,560 A | 8/1999 | Seper et al. |
| 6,544,499 B1 | 4/2003 | Glenn, Jr. et al. |
| 7,652,107 B2 | 1/2010 | Gallucci et al. |
| 7,652,162 B2 | 1/2010 | Silvi et al. |
| 8,110,648 B2 | 2/2012 | Hagemeister et al. |
| 9,308,668 B2 * | 4/2016 | Delis ............... B27K 3/153 |
| 2004/0156806 A1 * | 8/2004 | Patil ............... A61K 8/891 |
| | | 424/70.12 |
| 2007/0129520 A1 | 6/2007 | Ochs et al. |
| 2008/0161500 A1 | 7/2008 | Stark et al. |
| 2009/0137764 A1 | 5/2009 | Sutton et al. |
| 2009/0165812 A1 | 7/2009 | Resnick et al. |
| 2009/0211593 A1 | 8/2009 | Coppola et al. |
| 2012/0031420 A1 | 2/2012 | Gormley et al. |
| 2013/0204006 A1 | 8/2013 | Richard et al. |
| 2014/0127523 A1 * | 5/2014 | Delis ............... B27K 3/153 |
| | | 428/541 |
| 2017/0321003 A1 * | 11/2017 | Nakayama ............ C08G 64/085 |

* cited by examiner

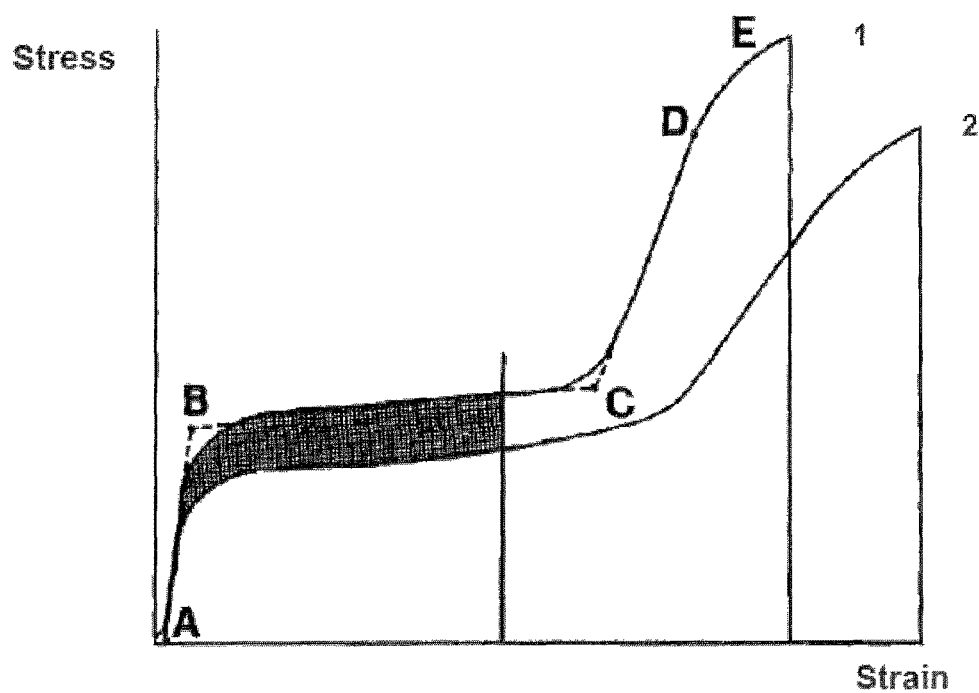
Example of a stress-strain curve of treated (2) and untreated hair (1)

SILICONE COMPOUNDS AND COMPOSITIONS THEREOF FOR THE TREATMENT OF AMINO ACID BASED SUBSTRATES

SUMMARY

This invention relates to silicone compounds and compositions thereof for treating amino acid based substrates. The silicone compounds according to the invention comprise 2 to 1000 siloxy units and at least one functional group selected from hydroxyaromatic, azetidine, thio ester, thio ether and methylol (—CH$_2$OH) groups. The invention further relates to compositions which comprise these functionalized silicones. The functionalized compounds of the present invention may be used in particular in hair care compositions.

TECHNICAL FIELD

The present invention relates to silicone compounds and compositions thereof which are used in particular for treating amino acid based substrates. The amino acid based substrates can include, for example, proteinaceous materials such as keratin, as found in human and animal hair, animal fur, finger and toe nails, various animal body parts, such as horns, hooves and feathers, other naturally occurring protein containing materials, such as wool; and synthetic polymers. Of particular interest are compositions, which deliver and attach the silicone compounds to human hair for permanent shaping purposes.

BACKGROUND OF THE INVENTION

Hair generally can be straight, wavy, curly, kinky or twisted. A human hair includes three main morphological components, the cuticle (a thin, outer-most shell of several concentric layers), the cortex (the main body of the hair), and, in case of higher diameter hair, the medulla (a thin, central core). The cuticle and cortex provide the hair strand's mechanical properties, that is, its tendency to have a wave, curl, or kink. A straight hair strand can resemble a rod with a circular cross-section, a wavy hair strand can appear compressed into an oval cross-section, a curly strand can appear further compressed into an elongated ellipse cross-section, and a kinky hair strand cross-section can be flatter still. The primary component of hair is the cross-linked, α-helix protein keratin. Keratins are intermediate filament proteins found specifically in epithelial cells, e.g. human skin and hair, wool, feathers, and nails. The α-helical type I and II keratin intermediate filament proteins (KIFs) with molecular weights around 45-60 kDa are embedded in an amorphous matrix of keratin-associated proteins (KAPs) with molecular weights between 20 to 30 kDa (M. A. Rogers, L. Langbein, S. Praetzel-Wunder, H. Winter, J. Schweizer, J. Int Rev Cytol. 2006; 251:209-6); both intra- and intermolecular disulfide bonds provided by cystines contribute to the cytoskeletal protein network maintaining the cellular scaffolding. In addition to the disulfide cross-links ionic bonding or salt bridges which pair various amino acids found in the hair proteins contribute to the hair strand's outward shape.

It is well known in the art that amino-acid based fibers, particularly hair, can be treated with functionalized silicones which deliver one or more cosmetic benefits, such as conditioning, color retention, shine and UV protection. Typically, these silicones are physically deposited on the fiber surface (cuticle) and therefore responsible for the outward appearance of the hair. They can be removed partially or completely by repeated washing processes. While the deposited silicones considerably improve the surface properties of the amino acid based fibers, i.e. smoothness and friction, they do not substantially impact the mechanical properties and the shape of the fibers.

People with naturally wavy, curly, or kinky hair may desire to reduce fizz and to get more control and a smoother appearance of their hairs. Several hair treatments including straightening methods are available, but these often involve the use of harsh and regulated substances.

Frequently used straightening preparations are based of sodium or potassium hydroxide blended with starch which are highly irritating to the scalp. Less irritating formulations are based on guanidine hydroxide or certain sulfites. Recent formulations are based on thio glycolic acid salts. The underlying principle is that under alkaline conditions disulfide bonds within the hair proteins undergo a reductive cleavage. The disulfide bonds are reduced to sulfhydryls and after shaping the desired hair configuration re-established by oxidation.

EP 295780, GB 1182939 and US 2012-0031420 propose to incorporate mercaptosilicones in this reduction/oxidation cycle. Target is a permanent conditioning effect. Disadvantages are the limited stability of the —SH moiety accompanied by an odor issue and the poor compatibility of these silicones with the aqueous carrier system.

The U.S. Pat. No. 5,679,619 proposes cystine modified silicones in combination with thioglycolates as reducing agent.

The U.S. Pat. No. 6,544,499 proposes silicones bearing protected —SH groups. Some of these protected systems are classified as being directly reactive towards —S—S— bonds whereas others need a reduction to —SH moieties. Disadvantage is the difficult synthesis of the protected structures.

The U.S. Pat. No. 5,935,560 describes thio and amino groups containing silicones which impart durable conditioning properties.

The different processes for straightening hairs have the tendency to weaken the strength of the hair. Therefore it is desirable to find compositions which enable straightening and recover strength and elasticity of the hair. Traditionally, aldehyde based formulations for a permanent hair shaping were developed. Most frequently formaldehyde is used for this so called Brazilian keratin shaping method (US 2012-0031420). The underlying principle is the crosslinking reaction between formaldehyde and keratin based amino and amido groups (H. Puchtler, Histochemistry, 82(1985), pp. 201-204) or between formaldehyde and —SH groups (US 2009-0211593) after straightening.

Dialdehydes, i.e. glyoxal, were proposed to replace formaldehyde (US 2009-0165812).

Silicones containing aldehyde functions are also proposed for personal care applications (US 2009-0137764), as cosmetic additive (US 2008-0161500) and more specifically for the permanent treatment of keratin fibers (US 2007-0129520). A disadvantage is the difficult synthetic process.

Methylol groups containing silicones were proposed for the treatment of cellulose based fibers (U.S. Pat. No. 3,432,536). In this case the polymer has the structure silicone-spacer-C(O)—NH—CH$_2$OH. Methylol groups containing silicones of the structure silicone-spacer-N(CH$_2$OH)—C(O)—R are proposed for the treatment of proteinacious fibers, i.e. hair (U.S. Pat. No. 8,110,648).

The U.S. Pat. No. 2,770,631 describes gallic acid modified silicones for sun screen and paint formulations. Resorcinol modified silicones were proposed as additives for polycarbonates in EP 2032624, EP 1951815 and as thermoplastic materials in GB 722822. WO 2007-078735 discloses the use of thioesters in rubber compounds.

DE 1111638 describes the synthesis of low molecular weight azetidinium compounds. Polymeric azetidinium derivatives are also known (H. Keul et. al., Macromolecules, 46, 638-646). Hydrocarbon based azetidinium compounds are used for the finishing of wool in the so called Hercosett process (EP 0236896).

None of the above prior art disclosures describes a straight forward synthetic methodology yielding stable and easy to formulate silicones which provide a benefit in a process for hair straightening with respect to a permanent hair shaping and hair strength without the usage of strongly irritating auxiliaries.

SUMMARY OF THE INVENTION

The present invention provides polyorganosiloxanes having an average number of 2 to 1000 siloxy units selected from the siloxy groups of the formulas:

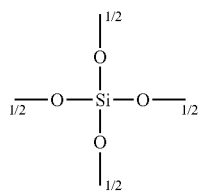
(Q)

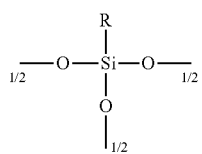
(T)

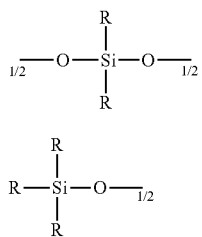
(D)

(M)

or silanes of the formula (I)

SiR$_4$     (I)

or silanes of the formula (II)

R$_3$Si—R$^3$—SiR$_3$     (II)

wherein
R is selected from R$^1$ and R$^F$, wherein
R$^1$ is selected from organic groups,
R$^F$ is selected from R$^{F1}$ and R$^{F2}$, wherein
R$^{F1}$ is selected from organic groups different from R$^1$ which contain at least one functional group F1 selected from an optionally substituted azetidine or azetidinium group and a methylol group, R$^{F2}$ is selected from organic groups different from R$^1$ which contain at least one functional group F2 selected from:
alkoxy silyl group,
amino group,
ammonium group,
phosphonium group,
epoxy group,
carbonate group,
urethane group,
isocyanate group, including blocked isocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
a mono-, di-, trihydroxy-substituted aromatic group,
mercapto group,
saccharide group,
polyether group with up to 60 carbon atoms,
thio ester and
thio ether group, and
R$^3$ is selected from divalent hydrocarbons radical which have up to 30 carbon atoms, and may contain optionally one or more groups selected from —O—, —NH—, —C(O)—, —C(S)—, tertiary amino groups

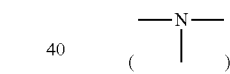

and quaternary ammonium groups

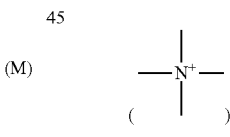

and wherein R$^3$ may optionally be substituted by one or more hydroxyl groups, with the proviso that R$^3$ is bound to the silicon atoms by a carbon atom,
with the proviso that R comprises at least one group R$^{F1}$.

BRIEF DESCRIPTION OF DRAWINGS

FIG. 1 shows an example of the different region in a stress-strain curve of hairs.

DETAILED DESCRIPTION OF THE INVENTION

In a preferred embodiment of the polyorganosiloxane of the invention the molar portion of the siloxanyl units which contain at least one radical R$^{F1}$ or R$^{F4}$ to all siloxanyl units of the polyorganosiloxane is 3.33 to 100 mol %, more preferred 5 to 100 mol %, even more preferred 5 to 50 mol %, most preferred 10 to 50 mol %.

In another preferred embodiment of the polyorganosiloxane of the invention the molar portion of the radicals $R^{F2}$ or $R^{F5}$ is 0 to 100 mol %, preferred 0 to 50 mol %, more preferred 0 to 30 mol %, specifically 0 to 10 mol %, more specifically 0 mol % based on the number of the radicals $R^{F1}$ or $R^{F4}$.

In another preferred embodiment of the polyorganosiloxane of the invention the portion of branching T and Q moieties is 0 to 50%, preferred 0 to 20%, more preferred 0 to 10%, specifically 0 to 5%, more specifically 0% based on the number of all siloxy units.

The average number on siloxy units in the polysiloxanes according to the invention is 2 to 1000, preferred 2 to 300, more preferred 2 to 30, even more preferred 2 to 20, even more preferred 2 to 15, specifically 2 to 12, more specifically 2 to 7. The average number on siloxy units can be determined i.e. by GPC (Gel Permeation Chromatography) using a system calibration versus polystyrene standards.

It is within the scope of the invention to use mixtures of different siloxanes according to the invention, mixtures of siloxanes and silanes according to the invention and mixtures of different silanes according to the invention.

Mixtures of polysiloxanes yield bi-, tri- and higher modal distributions. Bimodal mixtures having a bimodal distribution are preferred. One preferred embodiment of the invention is a mixture comprising short chained siloxanes bearing on average 2 to 15 siloxy units and longer chained siloxanes bearing on average 16 to 30 siloxy units. A mixture of this composition has the advantage that depending on the size of the molecules different locations within the hair structure can be modified with silicone polymers.

The organic radicals $R^1$ are preferably selected from the a group consisting of straight-chain, cyclic or branched, saturated, unsaturated or aromatic hydrocarbon radical which has up to 100 carbon atoms which optionally contain one or more groups selected from —O—, and which are optionally substituted by one more groups selected from the group consisting of hydroxyl, halogen (like chlorine, fluorine), a polyether radical with up to 60 carbon atoms, or two radicals $R^1$ from different siloxy moieties form a straight-chain, cyclic or branched, saturated, unsaturated or aromatic alkandiyl hydrocarbon radical which 2 to 20 carbon atoms between two silicon atoms, which are optionally substituted by one or more hydroxyl groups or halogen atoms, and are linked to silicon by a carbon atom. More preferably $R^1$ is selected from the group consisting of n-, iso-, or tert.-$C_1$-$C_{22}$-alkyl, $C_2$-$C_2$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which optionally can be each substituted by hydroxyl and halogen, and which optionally can contain one or more ether groups.

In the polyorganosiloxanes according to the invention $R^{F2}$ is preferably selected from hydrocarbon radicals which have up to 100 carbon atoms and may contain one or more groups selected from —O—, —S—, —$NR^2$—, in which $R^2$ is hydrogen, a monovalent, straight-chain, cyclic or branched, saturated, unsaturated or aromatic hydrocarbon radical which has up to 60 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —$NR^2$— groups is present, they may be the same or different, and wherein $R^{F2}$ contains at least one functional group F2. $R^{F2}$ is different from $R^1$ and different from $R^{F1}$. Preferably, $R^2$ is hydrogen, a saturated hydrocarbon radical with up to 24 carbon atoms, optionally containing one or two groups selected from —O—, —S—, —NH—, —C(O)— und —C(S)— and which may substituted by one or two hydroxyl groups.

$R^3$ is selected from divalent hydrocarbons radical which have up to 30 carbon atoms, and may contain optionally one or more groups selected from —O—, —NH—, —C(O)—, —C(S)—, tertiary amino groups

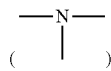

and quaternary ammonium groups

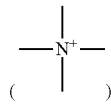

and wherein $R^3$ may optionally be substituted by one or more hydroxyl groups, with the proviso that $R^3$ is bound to the silicon atoms by a carbon atom, preferably, $R^3$ is a divalent saturated hydrocarbon radical with up to 20 carbon atoms, optionally containing one or two —O— groups, which may be substituted by hydroxyl and which is bound to silicon by a carbon atom.

Preferably, the radicals $R^1$ include: n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which can be substituted by one or more, preferred up to five, groups selected from hydroxyl and halogen, preferred fluorine, and can contain one or more ether groups, i.e. $H_3C$—, $CH_3CH_2$—, $CH_3CH_2CH_2$—, $(CH_3)_2CH$—, $C_8H_{17}$— and $C_{10}H_{21}$—, $H_2C=CH$—O—$(CH_2)_{1-6}$, cycloaliphatic radicals, i.e. cyclohexylethyl, limonyl, norbonenyl, phenyl, tolyl, xylyl, benzyl and 2-Phenylethyl, halogen($C_1$-$C_{10}$)alkyl, i.e. $C_fF_{fn+1}CH_2CH_2$— wherein f is 1 to 8, i.e. $CF_3CH_2CH_2$—, $C_4F_9CH_2CH_2$—, $C_6F_{13}CH_2CH_2$—,
$C_2F_5$—O($CF_2$—$CF_2$—O)$_{1-10}CF_2$—,
F[CF($CF_3$)—$CF_2$—O]$_{1-5}$—($CF_2$)$_{0-2}$—,
$C_3F_7$—OCF($CF_3$)— und
$C_3F_7$—OCF($CF_3$)—$CF_2$—OCF($CF_3$)—.

In a preferred embodiment $R^1$ is methyl, vinyl, phenyl, 3,3,3-trifluoropropyl, most preferred methyl.

$R^{F4}$ is selected from organic groups different from $R^1$ which contain at least one functional group F4 selected from
an optionally substituted azetidine or azetidinium group,
a methylol group,
a mono-, di-, trihydroxy-substituted aromatic group,
a thio ester and
a thio ether group.

Preferably the mono-, di-, trihydroxy-substituted aromatic groups have the structure:

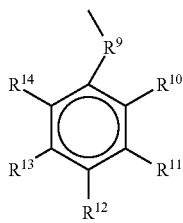

wherein $R^9 = R^3$ as defined above with an additional possibility of a substitution by nitrogen containing groups, preferred —NH$_2$, —NHR$^2$, —N(R$^2$)$_2$, therein R$^2$ is as defined above.

$R^{10}$, $R^{11}$, $R^{12}$, $R^{13}$, $R^{14}$ = $R^2$ as defined above with the proviso that 1 to 3 groups $R^{10}$ to $R^{14}$, preferred 1 to 2 groups, more preferred 1 or 2 or 3 groups are hydroxyl(—OH), preferably derived from allyl derivatives, i.e. 2-allyl-phenol, 4-allyl-phenol, 1-allyl-3,4-dihydroxybenzene, 1-allyl-2,6-dihydroxybenzene and 1-allyl-3-methoxy-4-hydroxybenzene (eugenol), mono hydroxy benzoic acids, i.e. 2-hydroxy benzoic acid, 3-hydroxy benzoic acid, 4-hydroxy benzoic acid, mono hydroxy cinnamic acids, i.e. 2-hydroxy cinnamic acid, 3-hydroxy cinnamic acid, 4-hydroxy cinnamic acid, dihydroxy benzoic acids or their partial esters, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, dihydroxy cinnamic acids or their partial esters, i.e. 3,4-dihydroxy cinnamic acid, trihydroxy benzoic acids or their partial esters, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, trihydroxy cinnamic acids or their partial esters, i.e. 3,4,5-dihydroxy cinnamic acid.

Preferably the optionally substituted azetidine or azetidinium group in the definition of $R^{F1}$ and $R^{F4}$ are selected from:

azetidine group of the structures

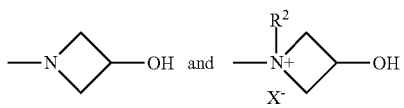

wherein $R^2$ is as defined above, preferably $R^2$ is hydrogen, a monovalent, straight-chain, cyclic or branched, saturated, unsaturated or aromatic hydrocarbon radical which has up to 20 carbon atoms and may contain one or more groups selected from —O—, —NH—, —C(O)— and —C(S)—, and which may optionally be substituted by one or more substituents selected from the group consisting of a hydroxyl group, more preferred $R^2$ is hydrogen, a monovalent, straight-chain, cyclic or branched, saturated, unsaturated or aromatic hydrocarbon radical which has up to 10 carbon atoms and may contain one or more groups selected from —O—, —NH—, —C(O)— and —C(S)—, and which may optionally be substituted by one or more substituents selected from the group consisting of a hydroxyl group, preferably selected from hydrogen, methyl, ethyl, n-propyl, i-propyl, n-butyl, cyclohexyl, morpholinyl, oligo ethylene oxide, oligo propylene oxide, oligo ethylene-propylene oxides, oligo ethylene-propylene-butylene oxides, $X^-$ is preferably chloride, bromide, iodide, preferred chloride.

The methylol group-comprising moieties in the definition of $R^{F1}$ and $R^{F4}$ are preferably selected from of the formulas:

—R$^3$—O—CH$_2$OH,

—R$^3$—N(R$^2$)(CH$_2$OH),

—R$^3$—N$^+$(R$^2$)$_2$(CH$_2$OH),

—R$^3$—N(CH$_2$OH)$_2$

—R$^3$—N$^+$(R$^2$)(CH$_2$OH)$_2$

—R$^3$—C(O)—NH—CH$_2$OH

—R$^3$—C(O)—N(CH$_2$OH)$_2$ wherein R$^3$ and R$^2$ are as defined above. Preferred R$^3$ is a divalent, straight-chain, cyclic or branched, saturated, unsaturated or aromatic hydrocarbon radical which has up to 15 carbon atoms, and may contain one or more groups selected from —O—, —NH—, —C(O)— and —C(S)—, quaternary ammonium and which may optionally be substituted by one or more substituents selected from the group consisting of a hydroxyl group, and bound to the silicon atom by a carbon atom, more preferred R$^3$ is a divalent, straight-chain, cyclic or branched, saturated, unsaturated or aromatic hydrocarbon radical which has up to 15 carbon atoms, and may contain one or more groups selected from —O—, —NH—, —C(O)— and —C(S)—, quaternary ammonium and which may optionally be substituted by one or more substituents selected from the group consisting of a hydroxyl group, and bound to the silicon atom by a carbon atom, even more preferred R$^3$ is a divalent, straight-chain, cyclic or branched, saturated, unsaturated or aromatic hydrocarbon radical which has up to 15 carbon atoms, and may contain one or more groups selected from —O—, —C(O)—, quaternary ammonium and which may optionally be substituted by one or more substituents selected from the group consisting of a hydroxyl group, and bound to the silicon atom by a carbon atom, preferably derived from hydroxyl phenyl, melaminyl and urea, under the proviso that radical R$^3$ does not comprise moieties of the structures —O—CH$_2$OH, —NH—CH$_2$OH and —N(CH$_2$OH)$_2$.

Preferably the methylol group-comprising moieties in the definition of $R^{F1}$ and $R^{F4}$ are of the formulas:

—R$^3$—O—CH$_2$OH,

—R$^3$—N(R$^2$)(CH$_2$OH),

—R$^3$—N$^+$(R$^2$)$_2$(CH$_2$OH),

—R$^3$—N(CH$_2$OH)$_2$

—R$^3$—N$^+$(R$^2$)(CH$_2$OH)$_2$

—R$^3$—C(O)—NH—CH$_2$OH

—R$^3$—C(O)—N(CH$_2$OH)$_2$

R$^3$ preferably comprises a moiety of the formula:

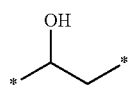

(wherein each * denote a bond).

Preferably the moiety of the formula:

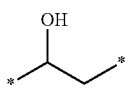

is formed by the ring opening reaction of an epoxide or carbonate group, wherein the epoxide or carbonate groups are preferably selected from:

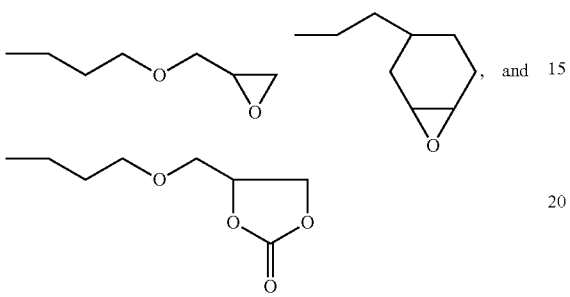

which groups are bound to the silicon atom of a siloxy group from the left side.

The thio ester group in the definition $R^{F4}$ is preferably of the structure $$—R^3—S—C(O)—R^2$$

and the thio ether group in the definition $R^{F4}$ is preferably of the structure:

$$—R^3—S—CH_2C(O)—R^2$$

wherein $R^2$ is as defined above, preferred $R^2$ is a monovalent, straight-chain, cyclic or branched, saturated, unsaturated or aromatic hydrocarbon radical which has up to 20 carbon atoms and may contain one or more groups selected from —O—, —NH—, —C(O)— and —C(S)—, and which may optionally be substituted by one or more substituents selected from the group consisting of a hydroxyl group, more preferred $R^2$ is a monovalent, straight-chain, cyclic or branched, saturated, unsaturated or aromatic hydrocarbon radical which has up to 10 carbon atoms and may contain one or more groups selected from —O—, —NH—, —C(O)— and —C(S)—, and which may optionally be substituted by one or more substituents selected from the group consisting of a hydroxyl group, even more preferred $R^2$ is methyl, ethyl, butyl, $R^3$ is as defined above, preferred $R^3$ is a divalent, straight-chain, cyclic or branched, saturated, unsaturated or aromatic hydrocarbon radical which has up to 15 carbon atoms, and may contain one or more groups selected from —O—, —NH—, —C(O)— and which may optionally be substituted by one or more substituents selected from the group consisting of a hydroxyl group, and bound to the silicon atom by a carbon atom, more preferred $R^3$ is a divalent, straight-chain, cyclic or branched, saturated, unsaturated or aromatic hydrocarbon radical which has up to 15 carbon atoms, and may contain one or more groups selected from —O—, —NH—, —C(O)— and which may optionally be substituted by one or more substituents selected from the group consisting of a hydroxyl group, and bound to the silicon atom by a carbon atom, even more preferred $R^3$ is a divalent, straight-chain, cyclic or branched, saturated, unsaturated or aromatic hydrocarbon radical which has up to 15 carbon atoms, and may contain one or more groups selected from —O—, —C(O)— and which may optionally be substituted by one or more substituents selected from the group consisting of a hydroxyl group, and bound to the silicon atom by a carbon atom.

Preferably, the optional functional groups F2 and F5 further improve the solubility of the polysiloxanes and silanes in the preferred solvent water. Additionally, they may strengthen the interaction with the proteinacious substrate.

The following functional groups F2 and F5 are especially preferred:
amino group,
ammonium group,
epoxy group,
carbonate group,
isocyanate group, especially blocked isocyanate group,
xanthogenate/xanthogenate ester group,
alkoxy silyl group
thiosulfato group.

Preferred optional radicals $R^{F2}$ and $R^{F5}$ are selected from the group consisting of:
quaternary phosphonium containing radicals of the formula $$—R^3—P^+(R^2)_3$$

wherein
$R^3$ as defined above and the P atom is bound to silicon by a carbon atom, radicals $R^2$ are as defined above, can be identical or different and preferably at least one radical $R^2$ is not hydrogen,
phosphine group containing radicals of the formula, $$—R^3—P(R^2)_2$$

wherein
$R^3$ as defined above and the P atom is bound to silicon by a carbon atom, radicals $R^2$ are as defined above, can be identical or different and preferably at least one radical $R^2$ is not hydrogen,
epoxy groups containing radicals selected from:

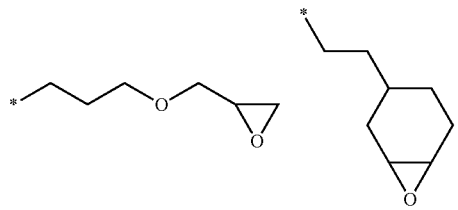 [SMILES: *CCCOCC1CO1 ; *CCC1CCC2OC2C1]

(wherein each * denote a bond),
carbonate groups containing radicals selected from:

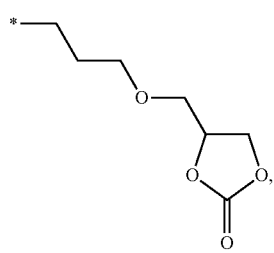 [SMILES: *CCCOCC1COC(=O)O1]

(wherein * denote a bond), urethane groups containing radicals selected from:
—R³—OC(O)NH—R², wherein R² and R³ as defined above,
urea groups containing radicals selected from:
—R³—NHC(O)NHR², wherein R² and R³ as defined above,
amide groups containing radicals selected from:
—R³—NHC(O)—R² or —R³—C(O)NH—R², wherein R² and R³ as defined above,
enamine groups containing radicals selected from:

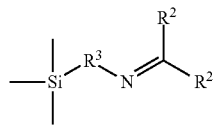

wherein R² are identical or different and R² and R³ as defined above, preferably synthesized from amino functional polysiloxanes and ketones, preferred aliphatic and aromatic ketones with up to 14 carbon atoms, more preferred aliphatic C3-C14 ketones, aromatic C8 to C12 ketones
enamine groups containing radicals selected from:

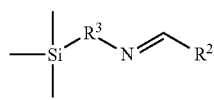

wherein R² and R³ as defined above, preferably synthesized from amino functional polysiloxanes and monoaldehydes, preferred aliphatic and aromatic aldehydes with up to 14 carbon atoms, more preferred aliphatic C1-C14 aldehydes, aromatic C7 to C11 aldehydes,
aldehyde groups containing radicals selected from:

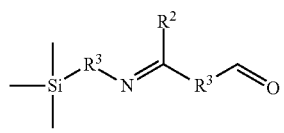

wherein R³ are identical or different and R² and R³ as defined above, preferably synthesized from aminofunctional polysiloxanes which are reacted with dialdehydes, i.e. glyoxal, malonic dialdehyde, succinic dialdehyde, phthalic dialdehyde, isophthalic dialdehyde, terephthalic dialdehyde,
zwitterionic groups containing radicals selected from:
carbobetaine groups containing radicals:

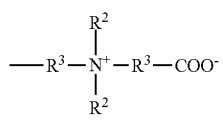

or their neutral form:

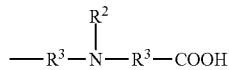

and salts thereof, wherein R² and R³ are identical or different and R² and R³ as defined above, sulphobetaine groups containing radicals:

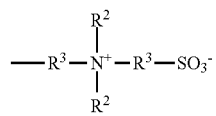

or their neutral form:

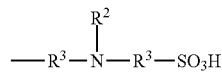

and salts thereof, wherein R² and R³ are identical or different and R² and R³ as defined above,
carboxylic acid or carboxylate groups containing radicals selected from:
—R³—COOR², —R³—COO⁻
wherein R² and R³ as defined above,
sulfonic acid or sulphonate groups containing radicals selected from:
—R³—SO₃R², —R³—SO₃⁻
wherein R² and R³ as defined above,
sulfuric acid half ester/sulfate groups containing radicals selected from:
—OSO₃R², —OSO₃⁻
wherein R² as defined above,
phosphoric acid ester/phosphate groups containing radicals selected from:

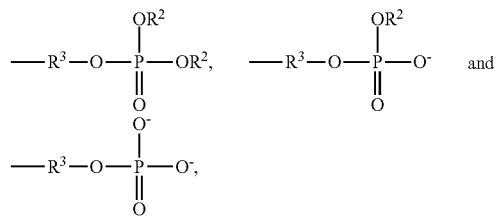

wherein R² and R³ as defined above,
fluoro phosphoric acid ester groups containing radicals selected from:

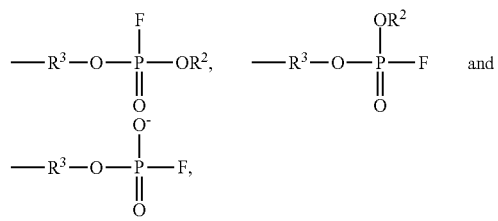

wherein R² and R³ as defined above,
phosphonic acid ester/phosphonate groups containing radicals selected from:

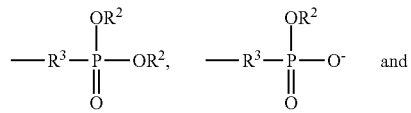

-continued

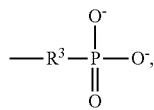

or their protonated forms, wherein $R^2$ and $R^3$ as defined above and with $R^3$ linked by a carbon atom to a P atom, phosphorous acid ester/phosphite groups containing radicals selected from:

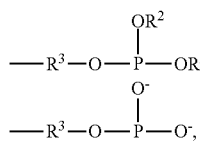

wherein $R^2$ and $R^3$ as defined above and linked by a carbon atom to the oxygen atom of the phosphorous acid ester/phosphite group, xanthogenate/xanthogenate ester groups containing radicals selected from:

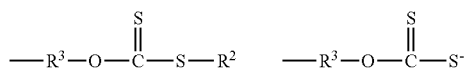

wherein $R^2$ and $R^3$ as defined above, and the cations neutralizing the anionic functional groups, selected from:

ammonium groups $(N^+(R^2)_4$, wherein $R^2$ as defined above, phosphonium groups $(P^+(R^2)_4$, wherein $R^2$ as defined above, as well as one to trivalent metal cations, and the anions neutralizing the cationic functional groups, selected from:

halogenide, hydroxide, borate, sulfate, phosphate, nitrate and carboxylate.

Details on the incorporation of the radicals $RF^2$ and $RF^5$ containing the groups F2 and F5 are described in WO 2012/143371.

In a preferred embodiment the polysiloxanes according to the invention contain at least one radical of the formula $M^F$:

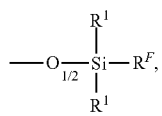

wherein $R^1$ and $R^F$ are as defined above,

In a preferred embodiment the polysiloxanes according to the invention are selected from the formulas:

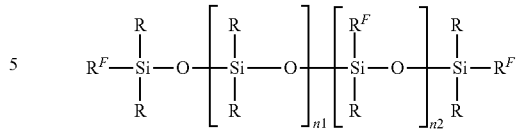

wherein

R is $R^1$, and $R^F$ is as defined above, with the proviso that at least one $R^F$ is $R^{F1}$, and the sum of the average numbers n1+n2 is 0 to 28, preferred 0 to 20, more preferred 0 to 15, even more preferred 5 to 15,

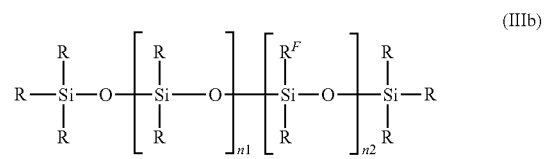

wherein

R is $R^1$, and $R^F$ is as defined above, with the proviso that at least one $R^F$ is $R^{F1}$, and the sum of the average numbers n1+n2 is 1 to 28, preferred 1 to 20, more preferred 1 to 15, even more preferred 5 to 15, with n2≥1, preferred 1 to 28, more preferred 1 to 10, even more preferred 1 to 5, with n2≥1,

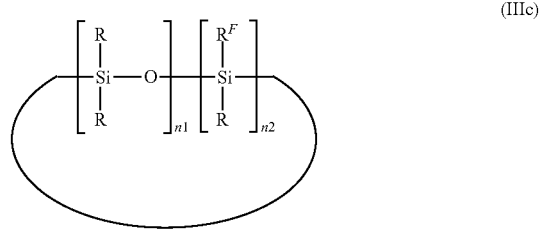

R is $R^1$, and $R^F$ is as defined above, with the proviso that at least one $R^F$ is $R^{F1}$, and wherein the sum of the average numbers n1+n2 is 3 to 7 with n2≥1, preferred n1+n2 is 1 to 7, more preferred 1 to 5, even more preferred 3 to 5.

The invention further refers to a method for treating amino acid based substrates, preferably for the treatment of hair, comprising the step of applying to such amino acid based substrate at least one polyorganosiloxane having an average number of 2 to 1000 siloxy units selected from the siloxy groups of the formulas:

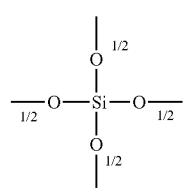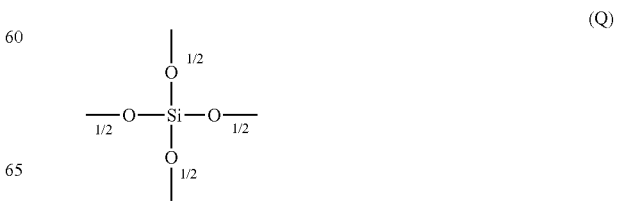

-continued

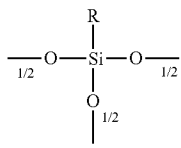
(T)

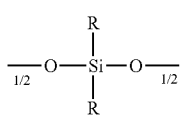
(D)

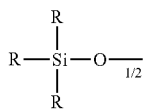
(M)

or at least one silane of the formula (I')

SiR$_4$ (I')

or at least one silane of the formula (II')

R$_3$Si—R$^3$—SiR$_3$ (II')

wherein
R is selected from R$^1$ and R$^{F3}$, wherein
R$^1$ is selected from organic groups,
R$^{F3}$ is selected from R$^{F4}$ and R$^{F5}$, wherein
R$^{F4}$ is selected from organic groups different from R$^1$ which contain at least one functional group F4 selected from
  an optionally substituted azetidine or azetidinium group,
  a methylol group,
  a mono-, di-, trihydroxy-substituted aromatic group,
  a thio ester and
  a thio ether group,
R$^{F5}$ is selected from organic groups different from R$^1$ which contain at least one functional group F5 selected from:
  alkoxy silyl group,
  amino group,
  ammonium group,
  phosphonium group,
  epoxy group,
  carbonate group,
  urethane group,
  isocyanate group, including blocked isocyanate group,
  urea group,
  amido group,
  aldehyde group,
  acetale or half acetale group,
  Schiff-Base or enamine group,
  zwitterionic group,
  carboxylic acid or carboxylate group,
  sulfonic acid or sulfonate group,
  sulfuric acid half ester or sulfate group,
  phosphoric acid ester or phosphate group,
  phosphonic acid ester or phosphonate group,
  phosphorous acid ester or phosphite group,
  xanthogenate/xanthogenate ester group,
  thiosulfato group,
  mercapto group,
  saccharide group, and
  polyether group with up to 60 carbon atoms, and
R$^3$ is selected from divalent hydrocarbons radical which have up to 30 carbon atoms, and may contain optionally one or more groups selected from —O—, —NH—, —C(O)—, —C(S)—, tertiary amino groups

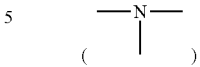

and quaternary ammonium groups

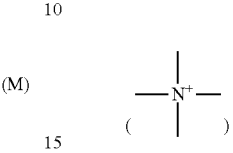

and wherein R$^3$ may optionally be substituted by one or more hydroxyl groups, with the proviso that R$^3$ is bound to the silicon atoms by a carbon atom,
with the proviso that R comprises at least one group R$^{F4}$.

Also for such method for treating amino acid based substrates the polyorganosiloxanes preferably have an average number of siloxy units of from 2 to 300. In such method for treating amino acid based substrates R$^1$ is as defined above. An the method for treating the amino acid based substrates according to the invention R$^{F5}$ is preferably selected from hydrocarbon radicals which have up to 100 carbon atoms and may contain one or more groups selected from —O—, —S—, —NR$^2$—, in which R$^2$ is hydrogen, a monovalent, straight-chain, cyclic or branched, saturated, unsaturated or aromatic hydrocarbon radical which has up to 60 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —NR$^2$— groups is present, they may be the same or different, and wherein R$^{F5}$ contains at least one functional group F5. In the method for treating amino acid based substrates according to the invention R$^{F4}$ is preferably selected from hydroxy-substituted azetidine and azetidinium groups. Further in the method for treating amino acid based substrates according to the invention R$^{F4}$ is preferably selected from azetidine and azetidinium groups of the following formulas:

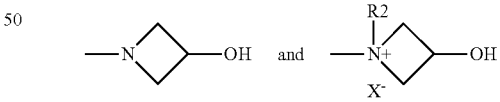

wherein R$^2$ is as defined above, and
X$^-$ is halogenide, and which azetidine or azetidinium groups are bound via a group R$^3$ to the silicon atom, wherein R$^3$ is as defined above. In the method for treating amino acid based substrates according to the invention R$^{F4}$ is preferably selected from methylol group-comprising moieties of the formulas:

—R$^3$—O—CH$_2$OH,

—R$^3$—N(R$^2$)(CH$_2$OH),

—R$^3$—N$^+$(R$^2$)$_2$(CH$_2$OH),

—R³—N(CH₂OH)₂

—R³—N⁺(R²)(CH₂OH)₂

—R³—C(O)—NH—CH₂OH

—R³—C(O)—N(CH₂OH)₂ wherein R³ is defined above, and preferably comprises a moiety of the formula:

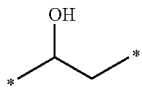

(wherein each * denotes a bond), which is preferably formed by the ring opening reaction of an epoxide or carbonate group, which are preferably selected from:

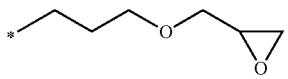

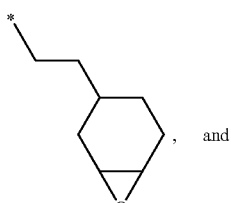

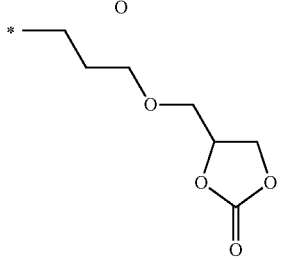

(wherein each * denote a bond),
which groups are bound to the silicon atom of a siloxy group from the left side.

In the method for treating amino acid based substrates according to the invention the polyorganosiloxanes preferably contain at least one siloxy group of the formula $M^F$:

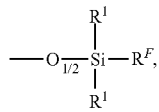

wherein $R^1$ is as defined above, and $R^F$ is $R^{F3}$ as defined above. In the method for treating amino acid based substrates the polyorganosiloxanes are preferably selected from the formulas:

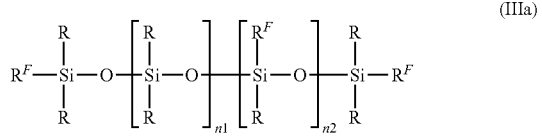

(IIIa)

wherein
R is $R^1$, and $R^F$ is as defined above, with the proviso that at least one $R^F$ is $R^{F1}$, and the sum of the average numbers n1+n2 is 0 to 28, preferred 0 to 20, more preferred 0 to 15, even more preferred 5 to 15,

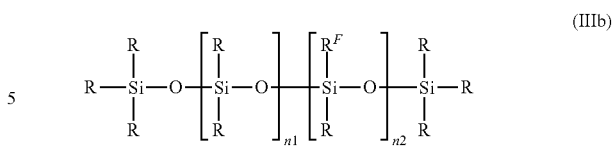

(IIIb)

wherein
R is $R^1$, and $R^F$ is as defined above, with the proviso that at least one $R^F$ is $R^{F1}$, and the sum of the average numbers n1+n2 is 1 to 28, preferred 1 to 20, more preferred 1 to 15, even more preferred 5 to 15, with n2≥1, preferred 1 to 28, more preferred 1 to 10, even more preferred 1 to 5, with n2≥1,

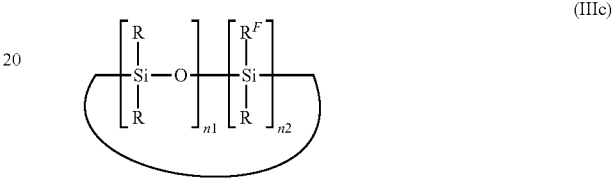

(IIIc)

R is $R^1$, and $R^F$ is as defined above, with the proviso that at least one $R^F$ is $R^{F1}$, and wherein the sum of the average numbers n1+n2 is 3 to 7 with n2≥1, preferred n1+n2 is 1 to 7, more preferred 1 to 5, even more preferred 3 to 5.

In a preferred embodiment the polysiloxanes according to the invention have averaged molecular weights Mw<2000 g/mol, preferred <1500 g/mol, more preferred <1000 g/mol, as determined by GPC using polystyrene as standard.

In a preferred embodiment of the invention more than one type of polysiloxanes according to the invention is used simultaneously.

It is preferred to combine the polysiloxanes according to the invention with functional polysiloxanes having functional group selected from amino, quaternary ammonium, and quaternary phosphonium groups alone or optionally in combination with anionic polysiloxane compounds having functional group selected from carboxylic acid/carboxylate, sulphonic acid/sulphonate, sulfuric acid half ester/sulphate, phosphoric acid ester/phosphate, phosphonic acid ester/phosphonate, phosphorous acid ester/phosphite, and xanthogenate/xanthogenate ester. Examples for the above mentioned compounds are described in WO 2012/143371. It is preferred to combine the polysiloxanes according to the invention with betaine functional polysiloxanes. Examples for these compounds are described in WO 2012/143371. It is further preferred to combine the polysiloxanes according to the invention with di- and polycationic compounds of the ABA or block copolymer type. Examples for these compounds are described in WO 02/10257, WO 02/10259 and DE 10036553.

Preferred precursors and intermediates are SiH functional, epoxy functional and carbonate functional polysiloxanes. The preparation of Si-functional polysiloxanes is described in the prior art (Silicone, Chemie und Technologie, Vulkan Verlag Essen 1989, S. 4). In one embodiment of the invention these SiH functional polysiloxanes are reacted with olefinically or acetylenically unsaturated hydroxyaromatic compounds yielding the target molecules by hydrosilylation.

The preparation of epoxy functional polysiloxane and silane intermediates is described in the prior art (Silicone, Chemie und Technologie, Vulkan Verlag Essen 1989, S. 90).

Preferred unsaturated epoxy precursors are allyl glycidyl ether, propargyl glycidyl ether and vinyl cyclohexene oxide. Preferably, these epoxy intermediates are reacted with amino, carboxylic acid or thiol functional precursors yielding the different target compounds.

In a preferred embodiment of the invention epoxy functional intermediates are reacted simultaneously or sequentially with precursors which introduce the radicals $R^{F2}$ and $R^{F5}$.

The preparation of carbonate functional polysiloxane and silane intermediates is described in the prior art. They can be synthesized from SiH functionalized polysiloxanes or silanes and unsaturated carbonate precursors, i.e. allyl carbonate (U.S. Pat. Nos. 5,672,338, 5,686,547). Alternatively, they can be prepared from epoxy functionalized precursors by $CO_2$ insertion (DE 19505892) or by reaction of aminosiloxanes or aminosilanes with bifunctional carbonate coupling agents (WO 2005/058863). Preferably, these carbonate intermediates are reacted with amino functional precursors yielding the different target compounds.

Preferred hydrocarbon based precursors for the incorporation of hydroxyaromatic radicals $R^{F2}$ and $R^{F4}$ are olefinically or acetylenically unsaturated derivatives, i.e. 2-allyl-phenol, 4-allyl-phenol, 1-allyl-3,4-dihydroxybenzene, 1-allyl-2,6-dihydroxybenzene and 1-allyl-3-methoxy,4-hydroxybenzene. These hydrocarbon based precursors can be used in hydrosilylations with SiH functionalized polysiloxane or silane precursors. Other preferred hydrocarbon based precursors for the incorporation of hydroxyaromatic radicals $R^{F2}$ and $R^{F4}$ contain carboxylic acid or amino groups. Preferred examples for carboxylic acid functionalized precursors are monohydroxy benzoic acids, i.e. 2-hydroxy benzoic acid, 3-hydroxy benzoic acid, 4-hydroxy benzoic acid, dihydroxy benzoic acids, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, trihydroxy benzoic acids, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid.

Other preferred examples for carboxylic acid functionalized precursors are mono hydroxy cinnamic acids, i.e. 2-hydroxy cinnamic acid, 3-hydroxy cinnamic acid, 4-hydroxy cinnamic acid, dihydroxy cinnamic acids or their partial esters, i.e. 3,4-dihydroxy cinnamic acid, trihydroxy cinnamic acids or their partial esters, i.e. 3,4,5-dihydroxy cinnamic acid, In a preferred embodiment of the invention these carboxylic acid functionalized hydrocarbon precursors are reacted with epoxy functionalized polysiloxane or silane intermediates. Optionally, a catalyst, for example a tertiary amine, i.e. triethylamine, is used (US 2012/0289649, example 1).

Preferred amino groups containing precursors are for example 3-(2-aminopropyl)phenol, 4-(2-aminopropyl)phenol, 3,4-dihydroxyphenylethylamine. Preferably, they are reacted with epoxy or carbonate functionalized polysiloxane or silane intermediates (DE 4318536, example 9; US 2011/0033411, example 4).

An example for carboxylic acid groups and amino groups containing precursors is tyrosine (DE 10036532, example 1).

The preferred hydrocarbon based precursor for the incorporation of azetidinyl radicals $R^{F1}$ or $R^{F4}$ is epichlorohydrine. Epichlorohydrine is preferably reacted with primary or secondary amino groups containing polysiloxanes or silanes yielding the corresponding cyclic tertiary amino or quaternary ammonium structures (DE 1111638, H. Keul et. al., Macromolecules, 46, 638-646). The corresponding primary and secondary amino groups containing polysiloxanes and silanes are described in the prior art. Preferably, they can be synthesized from SiH functionalized polysiloxane or silane precursors and unsaturated amines, for example allylamine, N-methyl-allylamine, hex-1-en-ylamine by hydrosilylation (R. Wagner et. al., Appl. Organomet. Chem., 1996, 10, 424). Alternatively, they can be synthesized from epoxy functionalized polysiloxane and silane precursors by reaction with ammonia or primary amino functions containing amines (DE 4318536, example 9). Examples for primary amino functions containing amines are methylamine, ethylamine, n-propylamine, i-propylamine, polyether based monoamino derivatives, for example EO/PO based M-Jeffamines (Huntsman Corp.), glucamine, aminoethylmorpholine, ethylene diamine, 1,2-propylene diamine, 1,3-propylenediamine, aminoethylethanolamine, aminoethylpiperazine. The utilization of i.e. primary-primary diamines and primary-secondary diamines opens up the possibility to incorporate more than one azetidinyl radical per anchoring point.

In another preferred embodiment of the invention tertiary amino functional azetidinyl modified polysiloxanes or silanes are synthesized from SiH functionalized polysiloxane or silane precursors and unsaturated tertiary amino functional azetidinyl intermediates (WO 2013/034705, example 2). An example is the tertiary amino functional reaction product of allylamine and epichlorohydrine

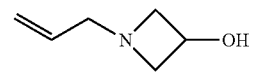

After hydrosilylation, the tertiary amino functionalized structure can be quatemized. Preferred alkylating agents are epoxides in the presence of acids, for example ethylene oxide, propylene oxide, butylenes oxide, allyl glycidyl ether, methacrylic acid glycidyl ester, phenyl gycidyl (DE 4318537, example 8). alkylhalides, for example alkyl chlorides, bromides, iodides, for example methyl chloride, ethylbromide, ethyl iodide, and haloalkyl acid esters, for example chloro acetic acid esters, for example chloro acetic acid ethyl ester (WO 2013/034705).

The preferred hydrocarbon based precursor for the incorporation of —$CH_2OH$ containing radicals $R^{F1}$ or $R^{F4}$ is formaldehyde.

In one preferred embodiment of the invention formaldehyde is reacted with hydroxyaromatic moieties containing polysiloxanes or silane derivatives. These derivatives can be synthesized, as described above, from epoxy functionalized polysiloxanes and silanes and carboxylic acid functionalized precursors, such as monohydroxy benzoic acids, i.e. 2-hydroxy benzoic acid, 4-hydroxy benzoic acid, dihydroxy benzoic acids, i.e. 2,4-dihydroxy benzoic acid, 2,6-dihydroxy benzoic acid, trihydroxy benzoic acids, i.e. 3,4,5-trihydroxy benzoic acid, by esterification.

In another preferred embodiment of the invention formaldehyde is reacted with the above described primary or secondary amino groups containing polysiloxane or silane derivatives.

In another preferred embodiment of the invention formaldehyde is reacted with amide groups containing polysiloxane or silane intermediates.

In one embodiment these amide groups containing intermediates can be synthesized from epoxy functional polysiloxanes and silanes and difunctional precursors bearing carboxylic acid as well as amide moieties by esterification. An example is succinic acid monoamide, HOOC—CH$_2$CH$_2$—C(O)NH$_2$.

In another embodiment of the invention amide groups containing intermediates can be synthesized from aminofunctional, preferably tertiary amino functional polysiloxanes and silanes and difunctional precursors bearing haloalkyl as well as amide moieties by alkylation. An example is chloroacetamide, ClCH$_2$C(O)NH$_2$. The preferred tertiary amino functional polysiloxane and silane intermediates can be synthesized for example from the corresponding expoxy intermediates and secondary amino functionalized precursors, for example dibutylamine, N-methylpiperazine and (CH$_3$)$_2$NCH$_2$CH$_2$CH$_2$NHCH$_2$CH$_2$CH$_2$N(CH$_3$)$_2$ (US 2009/-0142293, example 1). Methylol derivatives based on this synthetic protocol contain additional quaternary ammonium groups which improve the water solubility considerably.

The preferred hydrocarbon based precursor for the incorporation of thio ester radicals $R^{F4}$ or $R^{F2}$ of the structure —$R^3$—S—C(O)—$R^2$ are thio acetic acid and thio benzoic acid, wherein $R^2$ and $R^3$ are as defined above.

In a preferred embodiment epoxy functional polysiloxane and silane intermediates are reacted with thio acetic acid yielding the corresponding thio acetic acid esters (A. Z. Halimehjani et. al., Synthetic Communications, 2011, 41, 1638-1643).

The preferred hydrocarbon based precursor for the incorporation of thio ether radicals $R^{F4}$ or $R^{F2}$ of the structure —$R^3$—S—CH$_2$C(O)—$R^2$ are thio glycolic acid esters wherein $R^2$ and $R^3$ are as defined above.

In a preferred embodiment epoxy functional polysiloxane and silane intermediates are reacted with the thiol group of thio glycolic acid esters, preferably the methyl, ethyl and butyl esters, yielding the corresponding thio ethers of the thio glycolic acid esters (A. Babulreddy et. al., Int. J. of Res. in Org. Chem 2011, 1(1), 1-5; www.arkat-usa.org/get-file/ 23033/).

The invention also provides compositions for treating amino acid based substrates, preferrably the permanent shaping of human hair comprising
a) at least one polyorganosiloxane having an average number of 2 to 1000 siloxy units selected from the siloxy groups of the formulas:

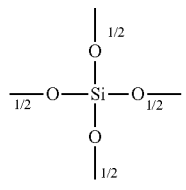

(Q)

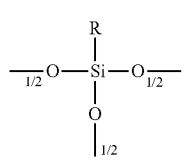

(T)

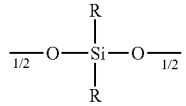

(D)

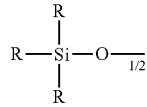

(M)

or at least one silane of the formula (I')

$$SiR_4 \qquad (I')$$

or at least one silane of the formula (II')

$$R_3Si—R^3—SiR_3 \qquad (II')$$

wherein
R is selected from $R^1$ and $R^{F3}$, wherein
$R^1$ is selected from organic groups,
$R^{F3}$ is selected from $R^{F4}$ and $R^{F5}$, wherein
$R^{F4}$ is selected from organic groups different from $R^1$ which contain at least one functional group F4 as defined above, $R^{F5}$ is selected from organic groups different from $R^1$ which contain at least one functional group F5 as defined above, and $R^3$ is as defined above, with the proviso that R comprises at least one group $R^{F4}$,
b) at least one diluent/solvent
c) optionally one or more protein, preferably keratin,
d) optionally one or more surface active ingredient/emulsifier,
e) optionally one or more emollient/fatty substance,
f) optionally one or more preservative,
g) optionally one or more skin protecting ingredient,
h) optionally one or more conditioning agent,
i) optionally one or more oxidizing agent,
j) optionally one or more reducing agent,
k) optionally one or more other auxiliary,
with the proviso that oxidizing agents and reducing agents are not present simultaneously in a given formulation.

Preferably, the formulations preferably the hair treating formulations comprise the following components:

| | Ingredient | Weight-% |
|---|---|---|
| a) | silicone actives according to component a) | 0.05 to 30 |
| b) | diluents/solvents | 5 to 99.95 |
| c) | protein, preferred keratin | 0 to 15 |
| d) | surface active ingredients/emulsifiers | 0 to 15 |
| e) | emollients/fatty substance | 0 to 15 |
| f) | preservatives | 0 to 5 |
| g) | skin protecting ingredients | 0 to 10 |
| h) | conditioning agents | 0 to 90 |
| i) | oxidizing agents agents | 0 to 10 |
| j) | reducing agents | 0 to 10 |
| k) | other auxiliary agents | 0 to 10 |

In a preferred embodiment of the invention the hair treating or shaping respectively formulations comprise the silicone actives in a concentration range from 0.05 to 30%, preferred 0.5 to 30%, more preferred 1 to 30%, even more preferred 1 to 20%, specifically 1 to 10%, wherein each percentage is per weight.

In a preferred embodiment of the invention the hair shaping formulations comprise the diluents/solvents in a concentration range from 5 to 99.95%, preferred 20 to 99.95%, more preferred 20 to 99%, even more preferred 30 to 99%, specifically 30 to 97% wherein each percentage is per weight.

In a preferred embodiment of the invention the hair shaping formulations comprise the optional protein, preferred keratin in a concentration range from 0 to 15%, preferred 0 to 10%, more preferred 0 to 5% wherein each percentage is per weight.

In a preferred embodiment of the invention the hair shaping formulations comprise the optional surface active ingredients in a concentration range from 0 to 15%, preferred 0 to 10%, more preferred 0 to 5% wherein each percentage is per weight.

In a preferred embodiment of the invention the hair shaping formulations comprise the optional emollents/fatty substance in a concentration range from 0 to 15%, preferred 0 to 10%, more preferred 0 to 5% wherein each percentage is per weight.

In a preferred embodiment of the invention the hair shaping formulations comprise the optional emulsifiers in a concentration range from 0 to 15%, preferred 0 to 10%, more preferred 0 to 5% wherein each percentage is per weight.

In a preferred embodiment of the invention the hair shaping formulations comprise the optional preservatives in a concentration range from 0 to 15%, preferred 0 to 10%, more preferred 0 to 5%, even more preferred 0 to 1%, specifically 0 to 0.1% wherein each percentage is per weight.

In a preferred embodiment of the invention the hair shaping formulations comprise the optional skin protecting ingredients in a concentration range from 0 to 15%, preferred 0 to 10%, more preferred 0 to 5%, even more preferred 0 to 1%, specifically 0 to 0.1% wherein each percentage is per weight.

In a preferred embodiment of the invention the hair shaping formulations comprise the optional conditioning agents in a concentration range from 0 to 15%, preferred 0 to 10%, more preferred 0 to 5%, even more preferred 0 to 1%, specifically 0 to 0.1% wherein each percentage is per weight.

In a preferred embodiment of the invention the hair shaping formulations comprise the optional oxidizing agents in a concentration range from 0 to 15%, preferred 0 to 10%, more preferred 0 to 5%, even more preferred 0 to 2% wherein each percentage is per weight.

In a preferred embodiment of the invention the hair shaping formulations comprise the optional reducing agents in a concentration range from 0 to 15%, preferred 0 to 10%, more preferred 0 to 5%, even more preferred 0 to 2% wherein each percentage is per weight.

Diluents/Solvents

The term "diluents/solvents" refers to substances that may be used to dilute/solvatize the silicone active according to the invention and the other optional other ingredients. Water is the preferred diluent/solvent. Suitable organic solvents are i.e. 2-methyl-1,3-propanediol, mono and dialcohols or the ethers thereof, in particular mono-C1-C3-alkyl ether, ethanol, n-propanol, isopropyl alcohol, tert. butanol, 1-methoxypropanol, 1-ethoxypropanol and ethoxydiglycol, diols and their esters 1,3- and 1,4-butanediol, pentylene glycol, hexylene glycol, diethyleneglycol and the monomethyl and monoethyl ether thereof, dipropylene glycol and the monomethyl and monoethyl ether thereof, glycerol, diglycerol, hexanetriol, sorbitol, ethyl carbitol, benzyl alcohol, benzyloxy ethanol, propylene carbonate, N-alkyl pyrrolidone. In a preferred embodiment water/ethanol and water/isopropyl alcohol mixtures are used. Generally, the addition of certain amounts of short chained alcohols improves the homogeneity of the formulations and the penetration of the formulations into the hair. Depending on the polymer structure type and the application purpose certain quantities on acids, bases and/or short chained alcohols are required in order to get transparent formulations. Suitable acids include inorganic or organic acids, like for example carboxyl acids, like acetic acid, hydrochloric acid, sulfuric acid, phosphoric acid.

Suitable bases include aqueous ammonia, alkaline hydroxides, carbonates etc.

Protein/Keratin

The optional protein, preferred keratin protein fractions used comprise of hydrolyzed keratin produced by alkaline and/or enzymatic hydrolysis using methods known in the art. The keratin hydrolysate is about 1,000-3,000 molecular weight. The keratin may be derived from human or other mammalian sources such as goat hair (US 2007-0048235), hoof or horn meals, (U.S. Pat. No. 6,555,505). Alternatively, "keratin protein fraction" is a purified form of keratin that contains predominantly, although not entirely, one distinct protein group as described in U.S. Pat. No. 7,148,327. Details on the keratin and keratin fractions are disclosed in US 2009-0165812.

Surface Active Ingredients/Emulsifiers

Another optional ingredient which may be included in these hair shaping formulations are surface active materials/emulsifiers. Surface active materials/emulsifiers are able to reduce the surface tension of water and cause the product to slip across or onto the skin and help to compatibilize the ingredients of the formulation. In one embodiment, the surfactants are amphoteric. Anionic or cationic surfactants may be used as well. Details on surface active ingredients/emulsifiers are disclosed in US 2009-0165812. Surfactants also include detergents and soap. Details on soaps are disclosed in WO 2012/027369.

Further examples of emulsifiers include:

Emulsifiers selected from among amphoteric, anionic, cationic and nonionic emulsifiers, which are used alone or as a mixture. The emulsifiers are appropriately selected according to the emulsion to be obtained (W/O or O/W). The emulsions may also contain stabilizers of other types, for instance fillers, gelling polymers or thickeners.

As emulsifying surfactants that may be used for the preparation of the W/O emulsions, examples include sorbitan, glycerol or sugar alkyl esters or ethers; silicone surfactants, for instance dimethicone copolyols, such as the mixture of cyclomethicone and of dimethicone copolyol, marketed under the trademark DC 5225 C by Dow Corning, and alkyldimethicone copolyols such as laurylmethicone copolyol marketed under the trademark Dow Corning 5200 Formulation Aid by Dow Corning; cetyldimethicone copolyol, such as the product marketed under the trademark Abil EM 90R by Goldschmidt, and the mixture of cetyldimethicone copolyol, of polyglyceryl isostearate (4 mol) and of hexyl laurate, marketed under the trademark Abil WE O9 by Goldschmidt. Other examples are the silicone emulsifiers from Momentive under the trademarks SF1528, SF1540, Silform EOF, Silform 60-A.

One or more co-emulsifiers may also be added thereto, which may be selected advantageously from the group comprising polyol alkyl esters.

Polyol alkyl esters that are especially exemplary include polyethylene glycol esters, for instance PEG-30 dipolyhydroxystearate, such as the product marketed under the trademark Aracel P135 by ICI.

Glycerol and/or sorbitan esters that are especially exemplary include, for example, polyglyceryl isostearate, such as the product marketed under the trademark Isolan GI 34 by Goldschmidt, sorbitan isostearate, such as the product marketed under the trademark Arlacel 987 by ICI, sorbitan glyceryl isostearate, such as the product marketed under the trademark Arlacel 986 by ICI, and mixtures thereof.

For O/W emulsions, examples of emulsifiers include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate marketed, for example, by ICI under the trademark Arlacel 165; oxyalkylenated (oxyethylenated and/or oxypropylenated) fatty alkyl ethers; sugar esters, for instance sucrose stearate; fatty alkyl ethers of sugars, especially polyalkylglucosides (APG) such as decylglucoside and laurylglucoside marketed, for example, by Henkel under the respective names Plantaren 2000 and Plantaren 1200, cetostearyl glucoside optionally as a mixture with cetostearyl alcohol, marketed, for example, under the trademark Montanov 68 by SEPPIC, under the trademark Tegocare CG90 by Goldschmidt and under the trademark Emulgade KE3302 by Henkel, and also arachidyl glucoside, for example in the form of a mixture of arachidyl alcohol, behenyl alcohol and arachidyl glucoside, marketed under the trademark Montanov 202 by SEPPIC. Examples of silicones emulsifiers, suitable for O/W emulsions are the polyether siloxane copolymers under the trademarks, SF1188A, SF1288, Silsoft 880, Silsoft 860, Silsoft 440, Silsoft 895, Silsoft 900.

Further emulsion stabilizers that will be used more particularly are isophthalic acid or sulfoisophthalic acid polymers, and in particular phthalate/sulfoisophthalate/glycol copolymers, for example the diethylene glycol/phthalate/isophthalate/1,4-cyclohexanedimethanol copolymer (INCI name: Polyester-5) marketed under the trademark Eastman AQ Polymer (AQ35S, AQ38S, AQ55S and AQ48 Ultra) by Eastman Chemical.

Other suitable emulsifiers are the amino-based emulsifiers, such as sodium stearoyl glutamate and phospholipids such as lecithin, hydroxylated lecithin.

Emollients, Fatty Substances

A further optional ingredient of the hair shaping formulations are one or more emollients. An "emollient" is a material that protects against wetness or irritation, softens, soothes, supples, coats, lubricates, moisturizes, protects and/or cleanses the skin. Emollients used comprise one or more of: a silicone compound, i.e. dimethicones, cyclomethicones, preferred D5 and D6 cyclo-siloxanes, dimethicone copolyols or mixtures of cyclomethicones and dimethicone/vinyldimethicone cross polymer), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. Details on emollients are disclosed in US 2009/0165812.

As fatty substances that are liquid at ambient temperature, often referred to as oils, that can be used in the invention, mention may be made of: hydrocarbon-based oils of animal origin, such as perhydrosqualene; hydrocarbon-based plant oils, such as liquid triglycerides of fatty acids containing 4 to 10 carbon atoms, for instance heptanoic or octanoic acid triglycerides, or else sunflower oil, maize oil, soya oil, grapeseed oil, sesame oil, apricot oil, macadamia oil, castor oil, avocado oil, caprylic/capric acid triglycerides, jojoba oil, shea butter; linear or branched hydrocarbons of mineral or synthetic origin, such as liquid paraffins and derivatives thereof, petroleum jelly, polydecenes, hydrogenated polyisobutene such as Parleam®; synthetic esters and ethers, in particular of fatty acids, for instance purcellin oil, isopropyl myristate, 2-ethylhexyl palmitate, 2-octyldodecyl stearate, 2-octyldodecyl erucate, isostearyl isostearate, hydroxylated esters, for instance isostearyl lactate, octyl hydroxystearate, octyldodecyl hydroxystearate, diisostearyl malate, triisocetyl citrate, fatty alcohol heptanoates, octanoates and decanoates; polyol esters, for instance propylene glycol dioctanoate, neopentyl glycol diheptanoate, diethylene glycol diisononanoate, pentaerythritol esters; fatty alcohols having 12 to 26 carbon atoms, for instance octyldodecanol, 2-butyloctanol, 2-hexyldecanol, 2-undecyl pentadecanol, oleyl alcohol; partially hydrocarbon-based and/or silicone-based fluoro oils; silicone oils, for instance volatile or non-volatile, linear or cyclic polydimethylsiloxanes (PDMS) which are liquid or pasty at ambient temperature (25° C.), such as cyclomethicones, dimethicones, optionally comprising a phenyl group, for instance phenyl trimethicones, phenyl trimethylsiloxydiphenylsiloxanes, diphenylmethyl-dimethyltrisiloxanes, diphenyl dimethicones, phenyl dimethicones, polymethylphenylsiloxanes; mixtures thereof. Details on suitable fatty substances are disclosed in WO 2012-038334.

Preservatives

Optionally, one or more preservatives may be included in the hair shaping formulations. Examples of such preservatives comprise one or more glycerin containing compound (e.g., glycerin or ethylhexylglycerin or phenoxyethanol), benzyl alcohol, EDTA, potassium sorbate and/or grapefruit seed extract. In a preferred embodiment, the hair straightening formulations are paraben free. Details on preservatives are disclosed in US 2009/0165812. Further suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium chloride, and methylbenzethonium chloride. Cosmetic chemists are familiar with appropriate preservatives and routinely choose them to satisfy the preservative challenge test and to provide product stability. Suitable preservatives are benzyl alcohol, mixture of ethylhexylglycerin with benzyl alcohol, 2-bromo-2 nitropropane 1,3 diol, disodium EDTA, phenoxyethanol, mixture of phenoxyethanol and ethylhexylglycerin, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Skin Protecting Agents

Optionally, the hair shaping formulations comprise one or more skin protecting agents. Skin protecting agents comprise one or more agents that prevent the undesired transmission of microbes or organic/inorganic chemicals. Details on skin protecting agents are disclosed in US 2009/0165812.

Conditioning Agents

Optionally, one or more conditioning agent may be included in the hair shaping formulations. In one preferred embodiment silicone based conditioning agents are incorporated. Preferred materials are PDMS grades ranging from 10 to 1,000,000 mPa·s, C2 to C18-alkyl derivatized silicones, dimethiconols, polyether modified silicones, amino groups or quaternized ammonium groups containing silicones. They may be also selected from polyorganosiloxanes having functional groups F2 or F5 as defined above. These silicones can be incorporated as neat materials, organic solutions, emulsions or microemulsions. Examples for amino groups containing silicones are aminoethylaminopropyl substituted silicones and aminopropyl substituted silicones. A commercially available example is the aminosilicone based emulsion SME 253 (Momentive Performance Materials). Details on quaternary ammonium groups containing silicones are i.e. disclosed in WO 02/10256, WO 02/10257 and WO 02710259. A commercially available example is the microemulsion Silsoft Q (Momentive Performance Materials). They impart a smooth and silky feel to hair. Alternatively, hydrocarbon based conditioning agents can be included. Details on these cationic type of material, containing amino and/or quaternary ammonium groups are disclosed in US 2009/0000638 and WO 2012/027369. As used herein, "conditioning agent" is suitably understood to mean any agent whose function is to improve the cosmetic properties of the hair, for example, the softness, disentangling, feel, smoothness and static electricity.

The at least one conditioning agent that may be used in the present disclosure may be in liquid, semi-solid or solid form, for example, oils, waxes and gums.

Other useful non-limiting examples of the at least one conditioning agent may include synthetic oils such as polyolefins, plant oils, fluoro oils, perfluoro oils, natural and synthetic waxes, silicones, non-polysaccharide cationic polymers, compounds of ceramide type, cationic surfactants, fatty amines, saturated fatty acids and esters of fatty acids other than those of the disclosure, and mixtures thereof.

The synthetic oils that may be used in the present disclosure may, in at least one embodiment, be chosen from polyolefins, for example, poly-α-olefins and further for example, hydrogenated or non-hydrogenated polybutene type, for instance, hydrogenated or non-hydrogenated polyisobutene type.

In at least one embodiment, isobutylene oligomers of molecular weight less than 1000 and mixtures thereof with polyisobutylenes of molecular weight greater than 1000, for example, ranging from 1000 to 15,000 are used.

Examples of poly-α-olefins include, but are not limited to those sold, for instance, under the name Permethyl 99 A, 101 A, 102 A, 104 A (n=16) and 106 A (n=38) by the company Presperse Inc., or alternatively the products sold, for example, under the name Arlamol HD (n=3) by the company ICI (n denoting the degree of polymerization), of hydrogenated or non-hydrogenated polydecene type.

Such products are sold, for example, under the names Ethylflo by the company Ethyl Corp. and Artamol PAO by the company ICI.

The animal or plant oils which may be used in at least one embodiment of the present disclosure may be chosen from, by way of non-limiting example, sunflower oil, corn oil, soybean oil, avocado oil, jojoba oil, marrow oil, grapeseed oil, sesame oil, hazelnut oil, fish oils, glyceryl tricaprocaprylate, and plant or animal oils of formula $R_9COOR_{10}$ wherein $R_9$ is a higher fatty acid residue comprising from 7 to 29 carbon atoms and $R_{10}$ is a linear or branched hydrocarbon-based chain comprising from 3 to 30 carbon atoms, for example, alkyl or alkenyl, and further for example, purcellin oil.

Natural or synthetic essential oils such as *eucalyptus* oil, lavandin oil, lavender oil, vetiver oil, *Litsea cubeba* oil, lemon oil, sandalwood oil, rosemary oil, camomile oil, savory oil, nutmeg oil, cinnamon oil, hyssop oil, caraway oil, orange oil, geraniol oil, cade oil and bergamot oil may also be used.

According to at least one embodiment, the waxes are natural (animal or plant) or synthetic substances that are solid at ambient temperature (20°-25° C.). They are insoluble in water, soluble in oils and are capable of forming a water-repellent film.

For the definition of waxes, reference may be made to the document, P. D. Dorgan, Drug and Cosmetic Industry, December 1983, pp. 30-33.

The wax or waxes which may be used in the context of the present disclosure may be chosen, by way of non-limiting example, from carnauba wax, candelilla wax, alfalfa wax, paraffin wax, ozokerite, plant waxes such as olive tree wax, rice wax, hydrogenated jojoba wax or the absolute waxes of flowers such as the essential wax of blackcurrant flower sold by the company Bertin (France), animal waxes such as beeswaxes, or modified beeswaxes (cerabellina); other waxes or waxy starting materials which may be used are, for instance, marine waxes such as those sold by the company Sophim under the reference M82, and polyethylene waxes or polyolefin waxes in general.

In at least one embodiment, the conditioning agent may be chosen from cationic polymers and silicones.

Among the non-saccharide cationic polymers that may be used in the context of the present disclosure may be chosen, by way of non-limiting example, from all those already known in the art to improve the cosmetic properties of hair treated with detergent compositions, for instance, those described in European Patent Application No. 0 337 354 and in French Patent Application Nos. 2 270 846, 2 383 660, 2 598 611, 2 470 596 and 2 519 863.

As used herein, "cationic polymer" is understood to mean any polymer comprising cationic groups and/or groups that may be ionized into cationic groups.

Among the cationic polymers that may be used in the present disclosure, non-limiting mention may be made of those which contain primary, secondary, tertiary and/or quaternary amine groups capable of forming part of the main polymer chain or of being borne by a side substituent directly bound to the latter.

In at least one embodiment, cationic polymers that may be used herein, have a number-average molecular mass ranging from 500 to $5 \times 10^6$, for example, ranging from $10^3$ to $3 \times 10^6$.

Suitable cationic polymers may include, by way of non-limiting example, polymers of the polyamine, polyamino amide and polyquaternary ammonium type.

These polymers of the polyamine, polyamino amide and polyquaternary ammonium type that may be used herein, may be chosen, for example, from those described in French Patents Nos. 2 505 348 and 2 542 997. Among these polymers, the following may be cited:

(1) homopolymers or copolymers derived from acrylic or methacrylic esters or amides and comprising at least one unit of the following formulae:

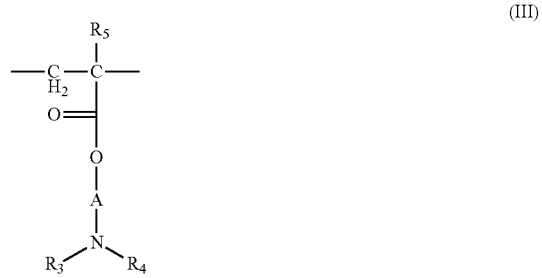

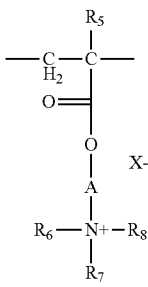

(IV)

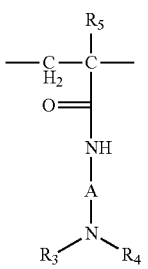

(V)

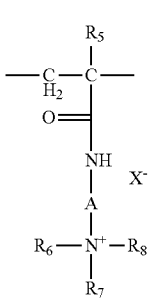

(VI)

wherein:

R$_3$ and R$_4$, which may be identical or different, are chosen from hydrogen and C$_1$-C$_6$ alkyl groups, for example, methyl or ethyl;

R$_5$, which may be identical or different, is chosen from hydrogen and a CH$_3$ radical; A, which may be identical or different, is chosen from linear and branched C$_1$-C$_6$ alkyl groups for example, ethyl or propyl or a hydroxy(C$_1$-C$_4$) alkyl group;

R$_6$, R$_7$ and R$_8$, which may be identical or different, are chosen from C$_1$-C$_{18}$ alkyl groups and a benzyl radical, for example, C$_1$-C$_6$ alkyl groups;

X is chosen from an anion derived from a mineral or organic acid, such as a methosulfate anion and a halide, such as chloride or bromide.

The copolymers of family (1) can also contain at least one unit derived from comonomers which may be chosen from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters. Examples of copolymers of family (1) that are suitable for use in accordance with the present disclosure include, but are not limited to:

copolymers of acrylamide and of dimethylaminoethyl methacrylate quatemized with dimethyl sulfate or with a dimethyl halide, such as those sold, for instance, under the name Hercofloc by the company Hercules, the copolymers of acrylamide and of methacryloyloxyethyltrimethylammonium chloride described, for example, in European Patent Application No. 0 80 976 and sold, for example, under the name Bina Quat P 100 by the company Ciba Geigy, the copolymer of acrylamide and of methacryloyloxyethyltrimethylammonium methosulfate sold, for instance, under the name Reten by the company Hercules, quatemized or non-quatemized vinylpyrrolidone/dialkylaminoalkyl acrylate or methacrylate copolymers, such as the products sold under the name Gafquat by the company ISP, for example, Gafquat 734 or Gafquat 755, or alternatively the products Copolymer 845, 958 and 937. These polymers are described in detail in French Patent Nos. 2 077 143 and 2 393 573, dimethylaminoethyl methacrylate/vinylcaprolactam/vinylpyrrolidone terpolymers, such as the product sold, for instance, under the name Gaffix VC 713 by the company ISP, vinylpyrrolidone/methacrylamidopropyldimethylamine copolymers sold, for example, under the name Styleze CC 10 by ISP, and quatemized vinylpyrrolidone/dimethylaminopropylmethacrylamide copolymers, such as the product sold, for instance, under the name Gafquat HS 100 by the company ISP.

(2) Polymers comprising piperazinyl units and divalent alkylene or hydroxyalkylene radicals comprising straight or branched chains, which may be interrupted by at least one atom chosen from oxygen, sulfur and nitrogen atoms or by aromatic or heterocyclic rings, as well as the oxidation and/or quaternization products of these polymers. These polymers are described in French Patent Nos. 2 162 025 and 2 280 361.

(3) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in an amount ranging from 0.025 mol to 0.35 mol per amine group of the polyamino amide; these polyamino amides can be alkylated or, if they comprise at least one tertiary amine functional group, they can be quaternized. These polymers are described in French Patent Nos. 2 252 840 and 2 368 508.

(4) The polyamino amide derivatives resulting from the condensation of polyalkylene polyamines with polycarboxylic acids followed by alkylation with difunctional agents, for example, adipic acid/dialkylaminohydroxyalkyldialkylenetriamine polymers wherein the alkyl radical comprise from 1 to 4 carbon atoms, for example, methyl, ethyl or propyl. These polymers are described in French Patent No. 1 583 363.

Among these derivatives, non-limiting mention may be made, for instance, of the adipic acid/dimethylaminohydroxypropyl/diethylenetriamine polymers sold, for example, under the name Cartaretine F, F4 or F8 by the company Sandoz.

(5) The polymers obtained by reaction of a polyalkylene polyamine comprising two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid ranges from 0.8:1 to 1.4:1; the polyamino amide that results from reaction with epichlorohydrin in a molar ratio of epichlorohydrin relative to the secondary amine group of the polyamino amide ranges from 0.5:1 to 1.8:1. These polymers are described in U.S. Pat. Nos. 3,227,615 and 2,961,347.

Polymers of this type are sold, for example, under the name Hercosett 57 by the company Hercules Inc. or alternatively under the name PD 170 or Delsette 101 by the company Hercules in the case of the adipic acid/epoxypropyl/diethylenetriamine copolymer.

(6) Cyclopolymers of alkyldiallylamine or of dialkyldiallylammonium, such as the homopolymers or copolymers comprising, as main constituent of the chain, units chosen from those of formulae (VII) and (VIII):

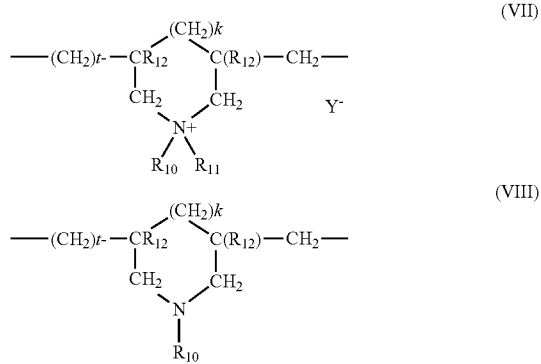

wherein:
k and t are 0 or 1;
the sum of k+t is 1;
$R_{12}$ is chosen from hydrogen and a methyl radical;
$R_{10}$ and $R_{11}$ are chosen from, independently of one another, $C_1$-$C_6$ alkyl groups, hydroxy ($C_1$-$C_5$) alkyl groups and a lower ($C_1$-$C_4$) amidoalkyl group, or $R_{10}$ and $R_{11}$ may form, together with the nitrogen atom to which they are attached, heterocyclic groups such as piperidyl or morpholinyl;
$Y^-$ is chosen from anions such as bromide, chloride, acetate, borate, citrate, tartrate, bisulfate, bisulfite, sulfate and phosphate. These polymers are described in French Patent No. 2 080 759 and in its Certificate of Addition 2 190 406.

According to at least one embodiment of the present disclosure, $R_{10}$ and $R_{11}$, independently of each other, may be chosen from $C_1$-$C_4$alkyl groups.

Among the polymers defined above, non-limiting mention may be made, for example, of the dimethyldiallylammonium chloride homopolymer sold, for instance, under the name Merquat 100 by the company Nalco (and its homologues of low weight-average molecular mass) and the copolymers of diallyldimethylammonium chloride and of acrylamide, sold, for example, under the name Merquat 550.

(7) The quaternary diammonium polymer comprising repeating units chosen from those of formula:

wherein:
$R_{13}$, $R_{14}$, $R_{15}$, and $R_{16}$, which may be identical or different, are chosen from aliphatic, alicyclic, arylaliphatic radicals comprising from 1 to 20 carbon atoms and lower hydroxyalkylaliphatic radicals, or alternatively $R_{13}$, $R_{14}$, $R_{15}$ and $R_{16}$, together or separately, form with the nitrogen atoms to which they are attached, heterocycles optionally comprising a second heteroatom other than nitrogen, or alternatively $R_{13}$, $R_{14}$, $R_{15}$ and $R_{16}$ are chosen from linear and branched $C_1$-$C_6$ alkyl radicals substituted with a nitrile, ester, acyl or amide group or a group —CO—O—$R_{17}$-D or —CO—NH—$R_{17}$-D wherein $R_{17}$ is an alkylene and D is a quaternary ammonium group; $A_1$ and $B_1$ are chosen from $C_2$-$C_{20}$ polymethylene groups which may be linear or branched, saturated or unsaturated, and which may comprise, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester groups, and $X^-$ is an anion derived from a mineral or organic acid;
$A_1$, $R_{13}$ and $R_{15}$ can form, with the two nitrogen atoms to which they are attached, a piperazine ring; in addition, if $A_1$ is a linear or branched, saturated or unsaturated alkylene or hydroxyalkylene radical, $B_1$ may comprise a group $(CH_2)_{np}$—CO-D-OC—$(CH_2)_p$—, wherein p is an integer ranging from 2 to 20,
wherein D is chosen from:
a) a glycol residue of formula: —O—Z—O—, wherein Z is chosen from linear and branched hydrocarbon-based radicals or a group corresponding to one of the following formulae:

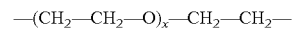

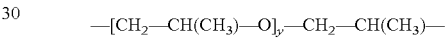

wherein x and y are decimals or integers ranging from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, wherein Y is chosen from linear and branched hydrocarbon-based radicals, or alternatively the divalent radical —$CH_2$—$CH_2$—S—S—$CH_2$—$CH_2$—;
d) a ureylene group of formula: —NH—CO—NH—.

In at least one embodiment, $X^-$ is an anion such as chloride or bromide.

The polymers which may be used in the context of the present disclosure may have a number-average molecular mass ranging from 1000 and 100,000.

These polymers are further described in French Patent Nos. 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In at least one embodiment, polymers that comprise repeating units corresponding to the formula (a) may be used:

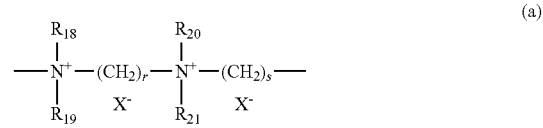

wherein:
$R_{18}$, $R_{19}$, $R_{20}$ and $R_{21}$, which may be identical or different, are chosen from $C_1$-$C_4$ alkyl groups or hydroxy($C_1$-$C_4$)alkyl radicals;
r and s are integers ranging from 2 to 20;
$X^-$ is an anion derived from a mineral or organic acid.

In another embodiment, a compound of formula (a) wherein $R_{18}$, $R_{19}$, $R_{20}$ and $R_{21}$ are methyl radicals and r is 3, s is 6 and X is Cl, referred to as hexadimethrine chloride according to the INCI nomenclature (CTFA) may be used.

(8) Polyquaternary ammonium polymers comprising units of formula (X):

$$\underset{X^-}{\overset{R_{22}}{\underset{R_{23}}{|}}}\!\!\!\!-\!\!\!\!\overset{}{\mathrm{N}^+}\!\!-\!\!(CH_2)_t\!-\!NH\!-\!CO\!-\!(CH_2)_u\!-\!CO\!-\!NH\!-\!(CH_2)_v\!-\!\underset{X^-}{\overset{R_{24}}{\underset{R_{25}}{|}}}\!\!\!\!-\!\!\!\!\overset{}{\mathrm{N}^+}\!\!-\!A\!-\!$$

(X)

wherein:

$R_{22}$, $R_{23}$, $R_{24}$ and $R_{25}$, which may be identical or different, are chosen from a hydrogen atom, a methyl, ethyl, propyl, β-hydroxyethyl, β-hydroxypropyl and a $-CH_2CH_2(OCH_2CH_2)_pOH$ radical, wherein p is 0 or an integer ranging from 1 to 6, with the proviso that $R_{22}$, $R_{23}$, $R_{24}$ and $R_{25}$ are not simultaneously hydrogen, t and u, which may be identical or different, are integers ranging from 1 to 6, v is 0 or an integer ranging from 1 to 34, $X^-$ is an anion, for example, halide, A is chosen from a divalent radical and $-CH_2-CH_2-O-CH_2-CH_2-$.

These compounds are described in European Patent Application No. 122 324.

In at least one embodiment, non-limiting mention may be made, for example, of Mirapol® A 15, Mirapol® AD1, Mirapol@ AZ1 and Mirapol® 175 sold by the company Miranol.

(9) Quaternary polymers of vinylpyrrolidone and of vinylimidazole, such as, the products sold under the names Luviquat® FC 905, FC 550 and FC 370 by the company BASF.

(10) Crosslinked methacryloyloxy($C_1$-$C_4$)alkyltri($C_1$-$C_4$) alkylammonium salt polymers such as the polymers obtained by homopolymerization of dimethylaminoethyl methacrylate quatemized with methyl chloride, or by copolymerization of acrylamide with dimethylaminoethyl methacrylate quatemized with methyl chloride, the homo- or copolymerization being followed by crosslinking with a compound containing olefinic unsaturation, for instance, methylenebisacrylamide. In at least one embodiment, the polymer may be a crosslinked acrylamide/methacryloyloxyethyltrimethylammonium chloride copolymer (20/80 by weight) in the form of a dispersion containing 50% by weight of the said copolymer in mineral oil. This dispersion is sold, for example, under the name Salcare® SC 92 by the company Ciba. In another embodiment, the polymer may be a crosslinked methacryloyloxyethyltrimethylammonium chloride homopolymer comprising about 50% by weight of the homopolymer in mineral oil or in a liquid ester. These dispersions are sold, for instance, under the names Salcare® SC 95 and Salcare® SC 96 by the company Ciba.

(11) Cationic polysaccharides, for example, celluloses and cationic galactomannan gums.

The cationic polysaccharides may, in at least one embodiment, be chosen from cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, are described in French Patent No. 1 492 597. These polymers are also defined, for instance, in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described in U.S. Pat. No. 4,131,576, such as hydroxyalkylcelluloses, for instance hydroxymethyl-, hydroxyethyl- or hydroxy-propylcelluloses grafted, for instance, with a methacryloylethyltrimethylammonium, methacrylamidopropyltrimethylammonium or dimethyldiallylammonium salt.

The cationic galactomannan gums are described in U.S. Pat. Nos. 3,589,578 and 4,031,307, for example, guar gums comprising trialkylammonium cationic groups and guar gums modified with a salt, for instance, chloride of 2,3-epoxypropyl-trimethylammonium.

Also suitable as cationic polymers are cationic proteins or cationic protein hydrolysates, polyalkyleneimines, for example, polyethyleneimines, polymers comprising vinylpyridine or vinylpyridinium units, condensates of polyamines and of epichlorohydrin, quaternary polyureylenes and chitin derivatives.

In at least one embodiment, the cationic polymers are chosen from cationic cyclopolymers, for example, the dimethyldiallylammonium chloride homopolymers or copolymers sold, for instance, under the names Merquat 100, Merquat 550 and Merquat S by the company Nalco, and quaternary vinylpyrrolidone and vinylimidazole polymers, cationic polysaccharides and mixtures thereof.

Suitable silicones that may be used in at least one embodiment of the present disclosure are polyorganosiloxanes that are insoluble in the composition and that may be in the form of oils, waxes, resins or gums.

The organopolysiloxanes are defined, for instance, in Walter Noll's "Chemistry and Technology of Silicones" (1968) Academic Press. They may be volatile or nonvolatile.

Cationic Proteins as Conditioners

In at least one embodiment, the cationic proteins or cationic protein hydrolysates are, for example, chemically modified polypeptides bearing quaternary ammonium groups at the end of the chain or grafted thereto. Their molecular mass can range, for example, from 1,500 to 10,000 and further for example, from 2,000 to 5,000. Examples of suitable cationic proteins or cationic protein hydrolysates include, but are not limited to:

collagen hydrolysates bearing triethylammonium groups, such as the products sold for instance, under the name Quat-Pro E by the company Maybrook and referred to in the CTFA dictionary as "Triethonium Hydrolyzed Collagen Ethosulfate";

collagen hydrolysates bearing trimethylammonium and trimethylstearylammonium chloride groups, sold, for example, under the name Quat-Pro S by the company Maybrook and referred to in the CTFA dictionary as "Steartrimonium Hydrolyzed Collagen";

animal protein hydrolysates bearing trimethylbenzylammonium groups such as the products sold, for instance, under the name Crotein BTA by the company Croda and referred to in the CTFA dictionary as "Benzyltrimonium hydrolyzed animal protein";

protein hydrolysates bearing, on the polypeptide chain, quaternary ammonium groups comprising at least one $C_1$-$C_{18}$ alkyl radical.

Examples of protein hydrolysates, sold by the company Croda, include, but are not limited to:

Croquat L wherein the quaternary ammonium groups comprise a $C_{12}$ alkyl group;

Croquat M wherein the quaternary ammonium groups comprise $C_{10}$-$C_{18}$ alkyl groups;

Croquat S wherein the quaternary ammonium groups comprise a $C_{18}$ alkyl group;

Crotein Q wherein the quaternary ammonium groups comprise at least one $C_1$-$C_{18}$ alkyl group.

Also useful herein are quatemized proteins or hydrolysates chosen from those of formula (XIV):

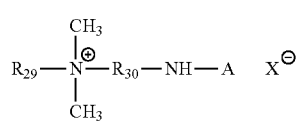

(XIV)

wherein:
X⁻ is chosen from an organic anion of an organic acid or an anion of a mineral acid;
A is a protein residue derived from hydrolysates of collagen protein;
$R_{29}$ is a lipophilic group comprising up to 30 carbon atoms; and
$R_{30}$ is a $C_1$-$C_6$ alkylene group. Non-limiting mention may be made, for example, of the products sold by the company Inolex under the name Lexein QX 3000, referred to in the CTFA dictionary as "Cocotrimonium Collagen Hydrolysate".

Non-limiting mention may also be made of quatemized plant proteins such as wheat, corn or soybean proteins: as quatemized wheat proteins, or for example, quatemized plant proteins sold by the company Croda under the names Hydrotriticum WQ or QM, referred to in the CTFA dictionary as "Cocodimonium Hydrolysed Wheat Protein", Hydrotriticum QL, referred to in the CTFA dictionary as "Lauridimonium Hydrolysed Wheat Protein" or Hydrotriticum QS, referred to in the CTFA dictionary as "Steardimonium Hydrolysed Wheat Protein".

Ceramides as Conditioners

According to at least one embodiment of the present disclosure, the compounds of ceramide type are, for example, natural or synthetic ceramides, glycoceramides, pseudoceramides and neoceramides.

Non-limiting examples of compounds of ceramide type are described, for example, in German Patent Application Nos. 4 424 530, 4 424 533, 4 402 929, 4 420 736, International Patent Application Nos. WO 95/23807, WO 94/07844, WO 94/24097, WO 95/16665, WO 94/10131, European Patent Application Nos. 0 646 572, 0 227 994 and French Patent Application No. 2 673 179, the teachings of which are included herein by way of reference.

Compounds of ceramide type used in at least one embodiment of the present disclosure may include:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol, for example, N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine,
and mixtures thereof.

Cationic Surfactants as Conditioners

Cationic surfactants that may also be used herein, include: optionally polyoxyalkylenated primary, secondary and tertiary fatty amine salts, quaternary ammonium salts, imidazoline derivatives, and amine oxides of cationic nature.

Non-limiting examples of quaternary ammonium salts may include:
those of general formula (XV):

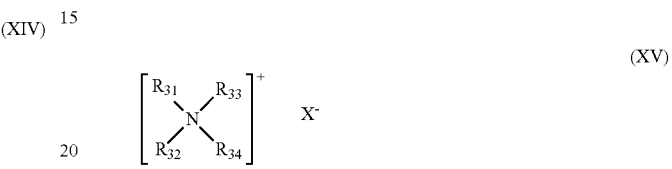

(XV)

wherein
$R_{31}$ to $R_{34}$, which may be identical or different, are chosen from $C_1$-$C_{30}$ linear and branched aliphatic radicals and aromatic radicals such as aryl or alkylaryl. The aliphatic radicals may comprise heteroatoms such as oxygen, nitrogen, sulfur and halogens. The aliphatic radicals are chosen, for example, from alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)allylacetate and hydroxyalkyl radicals, comprising from 1 to 30 carbon atoms;
X⁻ is an anion chosen from halides, phosphates, acetates, lactates, ($C_2$-$C_6$)alkyl sulfates, alkyl sulfonates and alkylaryl sulfonates;
quaternary ammonium salts of imidazolinium, such as, the salt of formula (XVI):

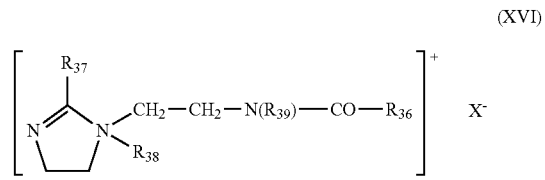

(XVI)

wherein
$R_{36}$ may be chosen from a $C_8$-$C_{30}$ alkenyl and $C_8$-$C_{30}$ alkyl radicals, for example, tallow fatty acid derivatives;
$R_{37}$ may be chosen from a hydrogen atom, $C_1$-$C_4$ alkyl radicals, $C_8$-$C_{30}$ alkenyl radicals and $C_8$-$C_{30}$ alkyl radicals;
$R_{36}$ is a $C_1$-$C_4$ alkyl radical, for example, a methyl radical;
$R_{39}$ is chosen from a hydrogen atom and $C_1$-$C_4$ alkyl radicals;
X⁻ is an anion chosen from halides, phosphates, acetates, lactates, alkyl sulfates, alkyl sulfonates and alkylaryl sulfonates;
$R_{36}$ and $R_{37}$ may be chosen from a mixture of $C_{12}$-$C_{21}$ alkenyl and $C_{12}$-$C_{21}$, alkyl radicals, for example, tallow fatty acid derivatives.

A non-limiting example is the product sold, for example, under the name "Rewoquat W 75" by the company Degussa;

diquaternary ammonium salts of formula (XVII):

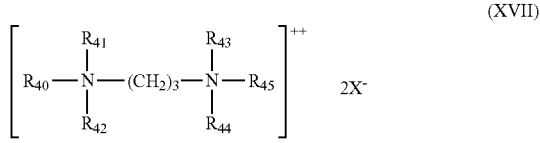

wherein:
$R_{40}$ is a $C_{16}$-$C_{30}$ aliphatic radical;
$R_{41}$, $R_{42}$, $R_{43}$, $R_{44}$ and $R_{45}$, which may be identical or different, are chosen from hydrogen or $C_1$-$C_4$ alkyl radicals; and
$X^-$ is an anion chosen from halides, acetates, phosphates, nitrates and methyl sulfates. A non-limiting example of diquaternary ammonium salts includes propane tallow diammonium dichloride;
According to at least one embodiment of the present disclosure, quaternary ammonium salts comprising at least one ester functional group that may be useful are, for example, those of formula (XVIII):

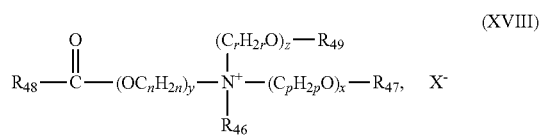

wherein
$R_{46}$ is chosen from $C_1$-$C_6$ alkyl radicals, $C_1$-$C_6$ hydroxyalkyl and dihydroxyalkyl radicals;
$R_{47}$ is chosen from:
a radical

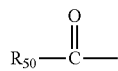

linear or branched, saturated or unsaturated $C_1$-$C_{22}$ hydrocarbon-based radicals $R_{51}$,
a hydrogen atom,
$R_{49}$ is chosen from:
a radical

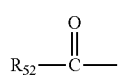

linear or branched, saturated or unsaturated $C_1$-$C_6$ hydrocarbon-based radicals $R_{53}$,
a hydrogen atom,
$R_{48}$, $R_{50}$ and $R_{52}$, which may be identical or different, are chosen from linear or branched, saturated or unsaturated $C_7$-$C_{21}$ hydrocarbon-based radicals;
n, p and r, which may be identical or different, are integers ranging from 2 to 6;
y is an integer ranging from 1 to 10;
x and z, which may be identical or different, are integers ranging from 0 to 10;
$X^-$ is a simple or complex organic or inorganic anion; and
with the proviso that the sum x+y+z is from 1 to 15, that when x is 0, then $R_{47}$ is $R_{51}$ and that when z is 0, then $R_{49}$ is $R_{53}$.

The $R_{46}$ alkyl radicals may be linear or branched and in at least one embodiment, linear.
$R_{46}$ may be a methyl, ethyl, hydroxyethyl or dihydroxypropyl radical and in at least one embodiment, a methyl or ethyl radical.
In at least one embodiment, the sum x+y+z is for example, from 1 to 10.
When $R_{47}$ is a hydrocarbon-based radical $R_{51}$, it may be long and comprise 12 to 22 carbon atoms, or short and comprise 1 to 3 carbon atoms.
When $R_{49}$ is a hydrocarbon-based radical $R_{53}$, it comprises 1 to 3 carbon atoms.
$R_{48}$, $R_{50}$ and $R_{52}$, which may be identical or different, are chosen from linear or branched, saturated or unsaturated $C_{11}$-$C_{21}$ hydrocarbon-based radicals. In another embodiment $R_{48}$, $R_{50}$ and $R_{52}$ may be chosen from linear or branched, saturated or unsaturated, $C_{11}$-$C_{21}$ alkyl and alkenyl radicals.
In at least one embodiment, x and z, which may be identical or different, are 0 or 1.
In another embodiment, y is 1.
In at least one embodiment, n, p and r, which may be identical or different, are 2 or 3.
The anion is, in at least one embodiment, chosen from a halide, for example, chloride, bromide and iodide, and an alkyl sulfate, for example, methyl sulfate. In another embodiment, methanesulfonate, phosphate, nitrate, tosylate, an anion derived from an organic acid, such as acetate or lactate, or any other anion that is compatible with the ammonium containing an ester functional group, may be used.
The anion $X^-$ is chosen, in at least one embodiment, from chloride or methyl sulfate.
In at least one embodiment, ammonium salts of formula (XVIII) may be used wherein
$R_{46}$ is a methyl or ethyl radical,
x and y are 1;
z is 0 or 1;
n, p and r are 2;
$R_{47}$ is chosen from:
a radical

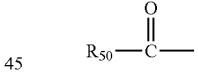

methyl, ethyl, $C_{14}$-$C_{22}$ hydrocarbon-based radicals;
and a hydrogen atom;
$R_{49}$ is chosen from:
a radical

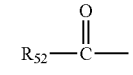

and a hydrogen atom;
$R_{48}$, $R_{50}$ and $R_{52}$, which may be identical or different, are chosen from linear or branched, saturated or unsaturated $C_{13}$-$C_{17}$ hydrocarbon-based radicals. In at least one embodiment, $R_{48}$, $R_{50}$ and $R_{52}$ are chosen from linear or branched, saturated or unsaturated $C_{13}$-$C_{17}$ alkyl and alkenyl radicals.
According to at least one embodiment, the hydrocarbon-based radicals are linear.
According to the present disclosure, the compounds of formula (XVI) may be chosen from, for example, diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts, for example, chloride or methyl sulfate, and mixtures thereof. The acyl radicals may comprise 14 to 18 carbon atoms and may be derived from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which may be oxyalkylenated, with fatty acids or with fatty acid mixtures of plant or animal origin, or by transesterification of the methyl esters thereof. This esterification is followed by a quaternization using an alkylating agent such as an alkyl halide, for example, methyl or ethyl halide, a dialkyl sulfate, for example, dimethyl or diethyl sulfate, methyl methanesulfonate, methyl para-toluenesulfonate, glycol chlorohydrin and glycerol chlorohydrin.

Such compounds are sold, for example, under the names Dehyquart by the company Cognis, Stepanquat by the company Stepan, Noxamium by the company CECA or Rewoquat WE 18 by the company Degussa.

The ammonium salts, which may comprise at least one ester functional group and may be used in the context of the present disclosure are further described in U.S. Pat. Nos. 4,874,554 and 4,137,180.

According to the present disclosure, non-limiting examples of quaternary ammonium salts of formula (XV) that may be used herein are chosen from tetraalkylammonium chlorides such as, dialkyldimethylammonium chlorides and alkyltrimethylammonium chlorides, wherein the alkyl radical comprises 12 to 22 carbon atoms, for example, behenyltrimethylammonium chloride, distearyidimethylammonium chloride, cetyltrimethylammonium chloride, and benzyldimethylstearylammonium chloride, or stearamidopropyldimethyl(myristyl acetate)ammonium chloride sold, for instance, under the name Ceraphyl 70 by the company Van Dyk.

Fatty Substances as Conditioners

The saturated fatty acids, in at least one embodiment, are chosen from myristic acid, palmitic acid, stearic acid, behenic acid and isostearic acid.

In a further embodiment, the fatty acid esters are chosen from carboxylic acid esters, for example, monocarboxylic esters, dicarboxylic esters, tricarboxylic esters and tetracarboxylic esters.

The monocarboxylic acid esters may, in at least one embodiment, be chosen from linear or branched, saturated or unsaturated $C_1$-$C_{26}$ aliphatic acid monoesters of linear or branched, saturated or unsaturated, $C_1$-$C_{26}$ aliphatic alcohols, wherein the total carbon number of these esters is greater than or equal to 10.

Suitable monoesters include, by way of non-limiting example, dehydroabietyl behenate, octyldodecyl behenate, isocetyl behenate; cetyl lactate, $C_{12}$-$C_{15}$ alkyl lactate, isostearyl lactate, lauryl lactate, linoleyl lactate, oleyl lactate, (iso)stearyl octanoate, isocetyl octanoate, octyl octanoate, cetyl octanoate, decyl oleate, isocetyl isostearate, isocetyl laurate, isocetyl stearate, isodecyl octanoate, isodecyl oleate, isononyl isononanoate, isostearyl palmitate, methylacetyl ricinoleate, myristyl stearate, octyl isononanoate, 2-ethylhexyl isononate, octyl palmitate, octyl pelargonate, octyl stearate, octyldodecyl erucate, oleyl erucate, ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isostearyl neopentanoate, and isodecyl neopentanoate.

Other esters useful herein include, by way of non-limiting example, $C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols.

In at least one embodiment, non-limiting mention may also be made of diethyl sebacate, diisopropyl sebacate, adipate, di-n-propyl adipate, dioctyl adipate, diisostearyl adipate, dioctyl maleate, glyceryl undecylenate, octyldodecylstearoyl stearate, pentaerythrityl monoricinoleate, pentaerythrityl tetraisononanoate, pentaerythrityl tetrapelargonate, pentaerythrityl tetraisostearate, pentaerythrityl tetraoctanoate, propylene glycol dicaprylate dicaprate, tridecyl erucate, trilsopropyl citrate, triisostearyl citrate, glyceryl trilactate, glyceryl trioctanoate, trioctyldodecyl citrate and trioleyl citrate.

Among the esters mentioned above, in at least one embodiment, the following non-limiting examples may be used herein: palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, and isodecyl neopentanoate.

Fluorinated Oils as Conditioners

The fluorinated oils are, for example, the perfluoropolyethers described in European Patent Application No. 486 135 and the fluorohydrocarbon compounds described in International Patent Application No. WO 93/11103, both of which are incorporated herein by way of reference.

As used herein, "fluorohydrocarbon compounds" is understood to mean compounds whose chemical structure comprises a carbon skeleton wherein certain hydrogen atoms have been replaced with fluorine atoms.

The fluorinated oils can also be fluorocarbons such as fluoroamines, for example, perfluorotributylamine, and fluorohydrocarbons, for example, perfluorodecahydro-naphthalene, fluoro esters and fluoro ethers.

The perfluoropolyethers are sold, for example, under the trade names Fomblin, by the company Montefluos and Krytox, by the company Du Pont.

Among the fluorohydrocarbon compounds that may be mentioned, are the esters of fluorine-containing fatty acids such as the product sold, for example, under the name Nofable FO by the company Nippon Oil.

The composition of the present disclosure may also comprise at least one mixture of conditioning agents.

Oxidizing Agents

Optionally, one or more oxidizing agent may be Included in the hair shaping formulations. Preferred oxidizing agents include organic oxidizers, i.e. benzoquinone, other quinone derivatives including hydroquinone and aminoquinones and suitable organic peroxides. Details on organic oxidizers are disclosed in US 2012/0031420 and WO 2012/027369.

Hydrogen peroxide is the preferred inorganic oxidizing agent. Persulfates, in the form of their sodium potassium and ammonium salts, may also be used alone or in combination with the hydrogen peroxide just before use. Other possible oxidizing agents include sodium percarbonate, sodium perborate, magnesium perborate, magnesium dioxide and barium dioxide. Details on these oxidizing agents are disclosed in U.S. Pat. No. 6,544,499.

Reducing Agents

Optionally, one or more reducing agent may be included in the hair shaping formulations with the proviso that oxidizing agents and reducing agents are not present simultaneously in a given formulation. Preferred reducing agents are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate (see also WO 93/1791), 1-3-propanediol monothioglycolate or the isomer mixture resulting therefrom, 1,3-butanediol and 1,4-butanediol monothioglycolate and the isomer mixtures therefrom, polyethylene glycol, such as di-, tri- and tetraethyleneglycol monothioglycolates, glycerol monothiolactate and further thio acids and the esters thereof, as well as mixtures thereof. Details on these organic reducing agents are disclosed in US 2009/0000638.

The usage of inorganic reducing sulfur compounds is basically also possible. Representative examples for use in the reducing compositions include cosmetically acceptable salts (e.g., alkali metal (e.g., sodium and potassium) and ammonium salts), esters (e.g., lower alkyl), amines (e.g., triethanolamine (TEA), monoethanolamine (MEA) and aminomethyl propanol (AMP), of sulfite, disulfite, bisulfite, metabisulfite, hydrosulfite, hyposulfite and pyrosulfite. Specific examples of suitable reducing agents thus include sodium metabisulfite, potassium metabisulfite, sodium sulfite, potassium sulfite, sodium thiosulfate, potassium thiosulfate, ammonium bisulfite, ammonium sulfite, ammonium metabisulfite, MEA sulfite, MEA metabisulfite, potassium bisulfite, sodium bisulfite, ammonium bisulfite, sodium hydrosulfite, potassium hydrosulfite, ammonium hydrosulfite, anhydrous sodium sulfite, diammonium sulfite, dipotassium disulfite, dipotassium pyrosulfite, AMP sulfite, AMP metabisulfite, TEA sulfite, TEA metabisulfite, sodium acid sulfite, sodium hyposulfite, sodium pyrosulfite, and sodium thiosulfate pentahydrate. Details on these inorganic reducing agents are disclosed in WO 2012/027369. Alternatively, high temperature and alkali, wherein the keratin is heated to around 100° C. or above, dithionites and certain hydrides can be used. Details on these reducing agents are disclosed in U.S. Pat. No. 6,544,499.

Additional Actives

Further, additional actives may be present in the compositions according to the invention. These additional active agents may be selected especially from among moisturizers, desquamating agents, agents for improving the skin barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipo-restructuring agents, slimming agents, agents for promoting the cutaneous capillary circulation, calmatives and/or anti-irritants, sebo-regulators or anti-seborrhoeic agents, astringents, cicatrizing agents, anti-inflammatory agents and anti-acne agents.

One skilled in this art will select the said active agent(s) as a function of the effect desired on the skin, the hair, the eyelashes, the eyebrows and the nails.

For caring for and/or making up aged skin, one will preferably select at least one active agent selected from among moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, and agents for promoting the cutaneous microcirculation for the area around the eyes.

The composition may also comprise at least one ingredient such as fillers with a soft-focus effect or agents for promoting the natural coloration of the skin, useful for complementing the biological effects of these active agents or for providing an immediate visual anti-aging effect. For caring for and/or making up greasy skin, one skilled in this art will preferably select at least one active agent selected from among desquamating agents, sebo-regulating agents or anti-seborrhoeic agents, and astringents.

The composition may also comprise at least one additional ingredient for complementing the biological effect of these active agents or for providing an immediate visual effect; especially exemplary are matting agents, fillers with a soft-focus effect, fluorescers, agents for promoting the naturally pinkish coloration of the skin, and abrasive fillers or exfoliants.

The composition of the present invention may have a low viscosity and can be used to formulate a wide variety of ingredients, such as fatty substances, humectants, solid particles, other silicones, organic or inorganic sunscreens, without the need of dispersants or emulsifiers.

In one embodiment there is provided a personal care application comprising a composition described herein.

In one further embodiment there is provided a hair care or skin care application comprising a composition described herein.

In one further embodiment there is provided a coating application, an oil extraction application, an agriculture application, or a lubrication application comprising a composition described herein.

Auxiliaries

The formulations may also comprise one or more additional auxiliaries, i.e. acids, bases and buffers to adjust the pH value, thickeners, structuring agents, fragrances and/or sunscreen agents, vitamines, pearlescent agents, gelling agents, trace elements, sequestering agents, antioxidants, anti-hair loss agents, antidandruff agents, propellants, ceramides, polymers, in particular film-forming polymers, and styling polymers; fillers, nacres, colorants and in particular pigments and dyes and also mixtures thereof.

Examples of Thickeners Include

Hydrophilic thickeners that are exemplary include carboxyvinyl polymers such as the Carbopol products (carbomers) and the Pemulen products (acrylate/$C_{10}$-$C_{30}$-alkylacrylate copolymer); polyacrylamides, for instance the crosslinked copolymers marketed under the trademarks Sepigel 305 (CTFA name: polyacrylamide/$C_{13-14}$ isoparaffin/Laureth 7) or Simulgel 600 (CTFA name: acrylamide/sodium acryloyldimethyttaurate copolymer/isohexadecane/polysorbate 80) by SEPPIC; 2-acrylamido-2- methylpropanesulfonic acid polymers and copolymers, which are optionally crosslinked and/or neutralized, for instance the poly(2-acrylamido-2-methylpropanesulfonic acid) marketed by Hoechst under the trademark Hostacerin AMPS (CTFA name: ammonium polyacryloyldimethyltaurate) or Simulgel 800 marketed by SEPPIC (CTFA name: sodium polyacryloyldimethyltaurate/polysorbate 80/sorbitan oleate); copolymers of 2-acrylamido-2-methylpropanesulfonic acid and of hydroxyethyl acrylate, for instance Simulgel NS and Sepinov EMT 10 marketed by SEPPIC; cellulose-based derivatives such as hydroxyethylcellulose; polysaccharides and especially gums such as xanthan gum; starch derivatives, associative thickeners and mixtures thereof.

Lipophilic thickeners that are exemplary include synthetic polymers such as poly(C10-C30 alkyl acrylates) marketed under the trademark Intelimer IPA 13-1 and Intelimer IPA 13-6 by Landec, or modified clays such as hectorite and its derivatives, for instance the products marketed under the trademark Bentone.

The compositions according to the invention may be formulated according to techniques that are well known to one skilled in this art. They may be in particular in the form of a simple or complex emulsion (O/W, W/O, O/W/O or W/O/W emulsion) such as a cream, a milk or a cream-gel; in the form of an aqueous gel; in the form of a lotion. They may optionally be packaged as an aerosol and may be in the form of a mouse or a spray.

The compositions according to the invention are preferably in the form of an oil-in-water or water-in-oil emulsion.

Examples of Film-Forming Polymers

According to preferred embodiments of the present invention, the compositions may comprise at least one additional film-forming polymer.

In the present invention, the term "film-forming polymer" means a polymer that is capable, by itself or in the presence of an auxiliary film-forming agent, of forming a macroscopically continuous deposit on keratin materials. The composition may comprise an aqueous phase, and the film-forming polymer may be present in this aqueous phase. In this case, it will preferably be a polymer in dispersion or an amphiphilic or associative polymer.

The term polymer in dispersion means water-insoluble polymers present in the form of particles of variable size. The polymer may or may not be crosslinked. The size of the polymer particles is typically between 25 and 500 nanometers and preferably between 50 and 200 nanometers. The following polymers in aqueous dispersion may be used: Ultrasol 2075 from Ganz Chemical, Daitosol 5000 AD from Daito Kasei, Avalure UR 450 from Noveon, DynamX from National Starch, Syntran 5760 from Interpolymer, Acusol OP 301 from Roehm & Haas, and Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Soltex OPT by the company Roehm & Haas, aqueous dispersions of acrylic or styrene/acrylic polymers sold under the brand name Joncryl® by the company Johnson polymer, or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer; the sulfopolyesters sold under the brand name Eastman AQ® by the company Eastman Chemical Products, and vinyl dispersions, for instance Mexomer PAM® from the company Chimex, and mixtures thereof, are other examples of aqueous dispersions of water-dispersible film-forming polymer particles.

The term "amphiphilic or associative polymers" means polymers comprising one or more hydrophilic parts that make them partially water-soluble and one or more hydrophobic parts via which the polymers associate or interact. The following associative polymers may be used: Nuvis FX 1100 from Elementis, Aculyn 22, Aculyn 44 and Aculyn 46 from Roehm & Haas, Viscophobe DB 1000 from Amerchol. Diblock copolymers formed from a hydrophilic block (polyacrylate or polyethylene glycol) and from a hydrophobic block (polystyrene or polysiloxane) may also be used.

The composition may comprise an oily phase and the film-forming polymer may be present in this oily phase. The polymer may then be in dispersion or in solution.

As examples of lipodispersible non-aqueous film-forming polymer dispersions in the form of non-aqueous dispersions of polymer particles in one or more silicone and/or hydrocarbon-based oils, which may be surface-stabilized with at least one stabilizer, especially a block, grafted or random polymer, mention may be made of acrylic dispersions in isododecane, for instance Mexomer PAP® from the company Chimex, and dispersions of particles of a grafted ethylenic polymer, preferably an acrylic polymer, in a liquid fatty phase, the ethylenic polymer advantageously being dispersed in the absence of additional stabilizer at the surface of the particles as described especially in document WO 04/055 081.

Among the film-forming polymers that may be used in the composition of the present invention, mention may be made of synthetic polymers, of free-radical type or of polycondensate type, and polymers of natural origin, and mixtures thereof.

The expression "free-radical film-forming polymer" means a polymer obtained by polymerization of unsaturated and especially ethylenically unsaturated monomers, each monomer being capable of homopolymerizing (unlike polycondensates).

The film-forming polymers of free-radical type may especially be vinyl polymers or copolymers, especially acrylic polymers.

The vinyl film-forming polymers may result from the polymerization of ethylenically unsaturated monomers containing at least one acidic group and/or esters of these acidic monomers and/or amides of these acidic monomers.

Monomers bearing an acidic group that may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid. The esters of acidic monomers are advantageously chosen from (meth) acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

The film-forming polymer may be chosen from block or random polymers and/or copolymers especially comprising polyurethanes, polyacrylics, silicones, fluoro polymers, butyl rubbers, ethylene copolymers, natural gums and polyvinyl alcohols, and mixtures thereof.

The vinyl film-forming polymers may also result from the homopolymerization or copolymerization of monomers chosen from vinyl esters and styrene monomers.

Examples of vinyl esters that may be mentioned are vinyl acetate, vinyl neodecanoate, vinyl pivalate, vinyl benzoate and vinyl t-butylbenzoate.

Styrene monomers that may be mentioned are styrene and α-methylstyrene.

Among the film-forming polycondensates that may be mentioned are polyurethanes, polyesteramides, polyamides, epoxyester resins, polyureas and polyesters.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of liposoluble film-forming polymers that may be mentioned include copolymers of a vinyl ester and of at least one other monomer that may be a vinyl ester, especially vinyl neodecanoate, vinyl benzoate and vinyl t-butylbenzoate, an α-olefin, an alkyl vinyl ether or an allylic or methallylic ester.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from copolymers of polyvinyl stearate, polyvinyl stearate crosslinked with the aid of divinylbenzene, of diallyl ether or of diallyl phthalate, polystearyl (meth)acrylate, polyvinyl laurate and polylauryl (meth)acrylate, it being possible for these poly (meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose.

A preferred at least one film forming polymer for use in the compositions of the present invention is chosen from copolymers of vinyl acetate and copolymers of vinylpyrrolidone such as allyl stearate/vinyl acetate copolymer, commercially available from Chimex under the trade name Mexomere PQ®, VP/hexadecene copolymer, commercially available from International Specialty Products (ISP) under the trade names Antaron® V 216 or Ganex® V 216, and VP/eicosene copolymer, commercially available from ISP under the trade names Antaron® V 220 or Ganex® V 220.

The at least one film-forming polymer may be present in the composition of the present invention in an amount ranging from about 0.1% to about 30% by weight; such as from about 0.5% to about 20% by weight; such as from about 1% to about 10% by weight based on the total weight of the composition, including all ranges and subranges therebetween.

Examples of Styling Polymers

The styling polymers may be chosen from nonionic, anionic, cationic, and amphoteric polymers and mixtures thereof. The styling polymer may additionally be halogenated, in particular fluorinated.

The styling polymers can be used in solubilized form or else in the form of dispersions of solid polymer particles (latex or pseudo-latex).

The nonionic styling polymers useful according to the present invention are polyurethanes and N-vinylpyrrolidone polymers and copolymers. Nonionic polymers containing N-vinylpyrrolidone in various weight average molecular weights are available commercially from ISP Corporation-specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Particularly preferred styling polymers are polyvinylpyrrolidone, vinylpyrrolidone/vinyl acetate copolymer, AMP-acrylates/allyl methacrylate copolymer (commercially available from Noveon under the tradename, Fixate G-100), sodium polystyrene sulfonate (commercially available from National Starch under the tradename, Flexan II), Vinylpyrrolidone/acrylates/lauryl methacyrlate copolymer (commercially available from ISP under the tradename, Acrylidone LM), polyquarternium-6, and polyurethane-2 (commercially available from Noveon under the tradename, Avalure 405 or 410).

The present invention further relates specifically to a method for treating amino acid based substrates, wherein the amino acid based substrates is hair.

(Hair in the context of the present invention may include apart from natural hair, hair that has been subjected already to a prior treatment, such as bleaching treatment, coloring treatment or any other prior common hair treatments (perm treatment, straightening treatment etc.).

Such method preferably, comprises the steps of
a) pretreatment of the hair with a reducing formulation comprising substances which break and transform —S—S-disulfide bridges into —SH thiol structures, (regarding the active ingredients of such reducing formulation it can be referred to the reducing agents indicated above)
b) application of the polysiloxanes or silanes according to the invention as defined above or the compositions comprising the same to the hair,
c) shaping of the hair, d) post-treatment of the hair after shaping with an oxidizing formulation comprising substances which accelerate the transformation of —SH thiol structures into —S—S-disulfide bridges (regarding the active ingredients of the oxidising agents it can be referred to the oxidising agents indicated above),
e) optional post-treatment of the hair after shaping with a complexing formulation, optionally including a post-treatment with an aqueous solution having an alkaline pH (>7, preferably about 8),
f) optional application of hair dyeing components.

In an alternative method of treating hair, the method comprises the steps of
a) hot ironing of the hair,
b) application of the polysiloxanes or silanes according to the invention as defined above or compositions comprising the same to the hair,
c) optional post-treatment of the hair after shaping with a complexing formulation, optionally including a post-treatment with an aqueous solution having an alkaline pH (>7, preferably about 8),
f) optional application of hair dyeing components.

In a further alternative method of treating hair it comprises the steps of
a) application of the polysiloxanes or silanes according to the invention as defined above or compositions comprising the same to the hair,
b) hot ironing of the hair,
c) optional post treatment of the hair after shaping with a complexing formulation, optionally including a post-treatment with an aqueous solution having an alkaline pH (>7, preferably about 8),
d) optional application of hair dyeing components.

It is thus within the scope of the invention to pretreat the hair with the polysiloxanes or silanes according to the invention as defined above or compositions comprising the same before shaping it with a reducing formulation. These reducing formulations comprise substances which break and transform —S—S-disulfide bridges into —SH thiol structures as mentioned above. Details on the application are disclosed for example in WO 2012/027369.

It is also within the scope of the invention to posttreat the hair after shaping with an oxidizing formulation. Oxidizing formulations comprise substances which accelerate the transformation of —SH thiol structures into —S—S— disulfide bridges.

Preferred oxidizing agents are disclosed in the section on oxidizing agents. Details on the application to the hair are disclosed in WO 2012/027369.

It is also within the scope of the invention to posttreat the hair after shaping with a complexing formulation. The term "complexing formulation" refers to formulations which comprise substances which may be used to form stable complexes between the derivatized polysiloxane and silane molecules and the complexing agent. It is also possible that keratin moieties within the hair structure are included into these complexes. Preferred polysiloxane and silane compounds according to the invention which are capable of interacting with such complexing formulation comprise hydroxyaromatic groups as described above for F2 and F4, preferred monohydroxy, dihydroxy and trihydroxy aromatic groups, i.e. hydroxyaromatic groups based on allyl derivatives, i.e. 2-allyl-phenol, 4-allyl-phenol, 1-allyl-3,4-dihydroxybenzene, 1-allyl-2,6-dihydroxybenzene and 1-allyl-3-methoxy-4-hydroxybenzene, benzoic acid derivatives, i.e. 2-hydroxy benzoic acid, 3-hydroxy benzoic acid, 4-hydroxy benzoic acid, dihydroxy benzoic acids, i.e. 2,3-dihydroxy benzoic acid, 2,4-dihydroxy benzoic acid, 2,5-dihydroxy benzoic acid, 2,6-dihydroxy benzoic acid, 3,4-dihydroxy benzoic acid, 3,5-dihydroxy benzoic acid, trihydroxy benzoic acids, i.e. 2,3,4-trihydroxy benzoic acid, 2,3,5-trihydroxy benzoic acid, 2,3,6-trihydroxy benzoic acid, 2,4,5-trihydroxy benzoic acid, 2,4,6-trihydroxy benzoic acid, 3,4,5-trihydroxy benzoic acid, mono hydroxy cinnamic acids, i.e. 2-hydroxy cinnamic acid, 3-hydroxy cinnamic acid, 4-hydroxy cinnamic acid, dihydroxy cinnamic acids or their partial esters, i.e. 3,4-dihydroxy cinnamic acid, trihydroxy cinnamic acids or their partial esters, i.e. 3,4,5-dihydroxy cinnamic acid.

Preferred complexing formulations comprise metal ions, i.e. derived from Na, K, Mg, Ca, Al, Zn, Co, Ti, Zr, Hf, V, Nb, Ta, Cr, Mo, W, Mn, Fe, Ru, Os, Cu, Ag, Au, Ni, Pd, Pt, the lanthanides, more preferred $Fe^{2+}$, $Fe^{3+}$, $Cu^{2+}$, $Al^{3+}$. Basic aspects of the complexation behaviour of low molecular weight hydroxyaromatic molecules with metal ions are disclosed within the prior art (Z. Xu, Nature, Science Reports, 3:2913, DOI 10.1038; R. I. L. Eggen et. al., Environm. Biology, 2001, 3(2), 81-91, S. Hussain et. al., IJETCAS, 13-148, 276-279; M. Saqib Qureshi et. al., J. Chem. Soc. Pak., 1998 (20), 3, 175-178).

In a preferred embodiment of the invention the hair shaping formulations according to the invention are applied before the hot iron straightening of curly hair or the hot iron curling of straight hair and impart a long lasting shaping effect as well as a noticeable smooth and silky feel to hair. Typically, the hair shaping formulations are allowed to stay on the hair for 5 to 60 minutes, preferred 10 to 50 minutes, more preferred 10 to 40 minutes.

Afterwards, a hot iron is applied to the hair which permanently bonds to or incorporates the silicones according to the invention into the hair. The elevated temperature can result in chemical reactions of the silicones according to the invention with reactive moieties of the keratin or in the formation of silicone-complexing agent complexes. Preferred temperatures range from 175° C. to about 235° C., more preferred from 180° C. to about 225° C., even more preferred from 190° C. to about 215° C. Typically, 2 to 10 rounds of hot ironing are applied in case of straightening or curling of the hair.

Based on the above said, the invention also provides a process for treating amino acid based substrates, preferably the permanent shaping of human hair comprising the steps
a) optional pretreatment of the hair before shaping with a reducing formulation comprising substances which break and transform —S—S-disulfide bridges into —SH thiol structures,
b) application of the formulations containing the polysiloxanes or silanes according to the invention,
c) hot iron straightening of curly hair or the hot iron curling of straight hair
d1) optional posttreatment of the hair after shaping with an oxidizing formulation comprising substances which accelerate the transformation of —SH thiol structures into —S—S— disulfide bridges or
d2) optional posttreatment of the hair after shaping with a complexing formulation comprising substances which can be used to form stable complexes between the derivatized polysiloxane and silane molecules and the complexing agent.

The invention also provides the use of the polysiloxanes or silanes according to the invention in all kind of hair treatments in particular but not limited to hair straightening treatment, hair conditioning treatment, hair shine treatment, hair UV protecting treatment, hair washing treatment, hair coloring treatment, permanent shaping treatment of hairs, protecting dyed hair color treatment, e.g. after hair wash, hair color retention treatment, hair color enhancement treatment, and/or reduced color fading treatment of artificially colored hair, like methods of protecting dyed hair color from fading or wash-out during exposure to air, light (e.g. UV-light) and/or shampooing/hair washing, methods for increasing color Intensity in hair coloring treatments, methods for improving color retention, in particular after wash, methods for providing enhanced color retention and/or reduced color fading of hair artificially colored with compositions having pigments.

In particular, it was found that the polysiloxanes or silanes according to the invention are useful in all kind of hair coloring treatments, since they protect dyed hair color, e.g. after hair wash, improve the hair color retention, and in particular lead to hair color enhancement and reduced color fading of artificially colored hair. In achieving these results the polysiloxanes or silanes according to the invention are preferably applied before hair coloring treatment, but they can be also applied after hair coloring treatment. In a preferred embodiment the present invention provides a method in hair coloring treatment, which comprises the steps of a) optionally pretreatment of the hair with an aqueous alkaline solution,
b) application of the polysiloxanes or silanes as defined above or the compositions comprising the same to the hair, and thereafter
c) the application of hair dyeing components to the hair.

Preferably steps a) and/or b), preferably step b), are carried out before step c). Preferably in step a) an alkaline aqueous solution is used having a pH of more than 7, preferably more than 8, still preferably more than 9, like e.g. 9 to 11, for example a sodium hydroxide solution.

It is within the scope of the invention to carry out the reactions for the production of the polysiloxane or silane compounds in accordance with the invention without solvents or in the presence of solvents. Suitable solvents are, for example, water, esters or ester moieties comprising solvents, such as ethyl acetate, butyl acetate, methoxypropyl acetate, ethylene glycol monobutyl ether acetate, diethylene glycol monobutylether acetate, butyrolactone, acetic acid ester of dicyclopentadiene, triglycerides such as caprylic/capric triglyceride and fatty acid esters such as cetearyl isononanoate, ethylhexyl palmitate or cetyl palmitate, ether or ether moieties comprising solvents, such as dibutyl ether, methyl ether of dicyclopentadiene, ethylene glycol monobutyl ether, dipropylene glycol, diethylene glycol, diethylene glycol monobutyl ether, propylene glycol monomethyl ether, dipropylene glycol monomethyl ether, dipropylene glycol monobutyl ether, dipropylene glycol dimethylether, tripropylene glycol dimethyl ether, alcohols, such as ethanol, 2-propanol, propylene glycol, 1,3-butane diol, hexylene glycol, caprylyl glycol, and glycerol, aromatic solvents, such as toluene, xylene, heteroelements containing solvents, such as N-methylpyrrolidone, N-octylpyrrolidone. The optional choice of a solvent and its required quantity are inter alia dependent on the solubility of the raw materials and target molecule in a given solvent as well as the intended application purpose. Thus, it can be advantageous to already perform the synthesis in a solvent, which is, for example, a component of the final hair treatment formulation.

It is within the scope of the invention to run the reaction in a single solvent or in solvent mixtures.

The reactions are preferably carried out in a temperature range between room temperature and 180° C., preferably room temperature and 150° C., most preferably 50° C. and 150° C.

The progress of the reactions can be i.e. monitored by means of suitable methods (IR, NMR, Titration).

EXAMPLES (The percentages usually refer to weight-%).

Example 1

Synthesis of a Dihydroxy Benzoic Acid Derivative 120.52 g propylene glycol mono methyl ether, 18.14 g (0.118 mol —COOH) 3,4-dihydroxy benzoic acid, 0.5 g triethylamine and 33.51 g (0.107 mol epoxy groups) of an epoxy functionalized silicone of the structure

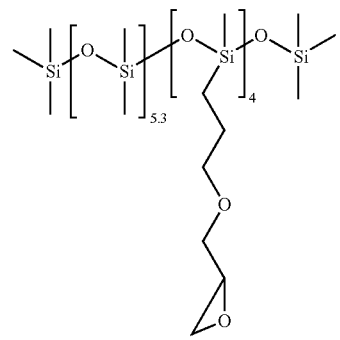

were mixed at room temperature and heated to 120° C. for 22 hrs. The conversion on epoxy groups was 100% (1H-NMR).

The solvent was removed at 65° C./20 mmHg. Afterwards, the material was washed twice with 25 ml n-hexane. The solvent was removed at 65° C./20 mmHg. A brownish opaque product of the structure

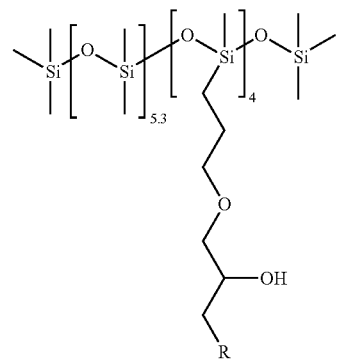

with R=

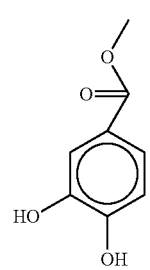

was obtained.

Example 2

Synthesis of a Trihydroxy Benzoic Acid Derivative 120.78 g propylene glycol mono methyl ether, 19.36 g (0.113 mol —COOH) 2,3,4-trihydroxy benzoic acid, 0.32 g triethylamine and 32.40 g (0.103 mol epoxy groups) of an epoxy functionalized silicone of the structure

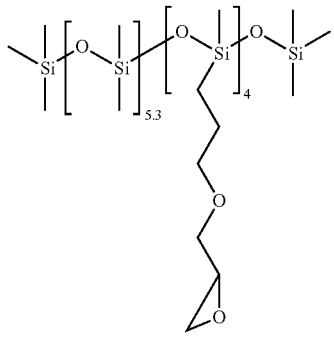

were mixed at room temperature and heated to 120° C. for 26 hrs. The conversion on epoxy groups was 98% (1H-NMR).

The solvent was removed at 65° C./20 mmHg. Afterwards, the material was washed twice with 25 ml n-hexane. The solvent was removed at 65° C./20 mmHg. A brownish opaque product of the structure

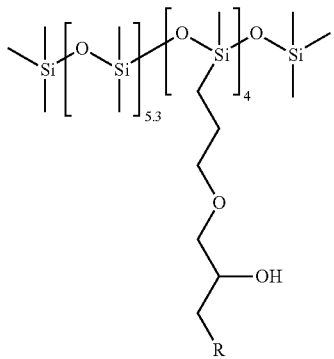

with R=

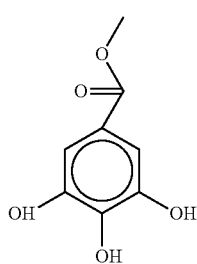

was obtained.

Example 3

Synthesis of an Azetidine Derivative 133.91 g 2-propanol, 6.36 g (0.107 mol —NH$_2$) isopropylamine, and 33.69 g (0.108 mol epoxy groups) of an epoxy functionalized silicone of the structure

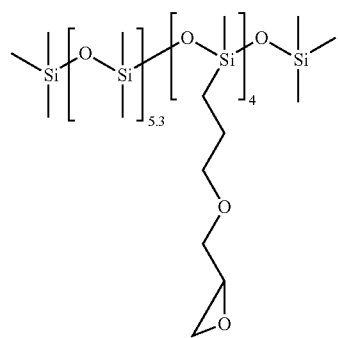

were mixed at room temperature and heated to reflux for 8 hrs. The conversion on epoxy groups was 100% (1H-NMR). The intermediate was cooled down to 40° C. A mixture consisting of 33.48 g 2-propanol and 9.95 g (0.107 mol epoxy and —Cl) of epichlorhydrin was added during 10 minutes. The mixture was heated to reflux for 12.5 h.

The solvent was removed at 50° C./20 mmHg. Afterwards, the material was washed twice with 25 ml n-hexane. The solvent was removed at 50° C./20 mmHg. A yellowish opaque product of the structure

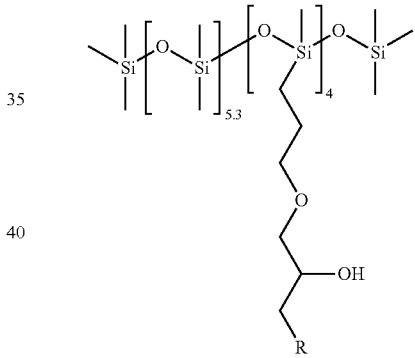

with R=

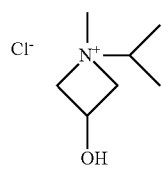

was obtained.

Example 4

Synthesis of an Azetidine Derivative 133.2 g 2-propanol, 6.36 g (0.107 mol —NH$_2$) n-propylamine, and 33.69 g (0.108 mol epoxy groups) of an epoxy functionalized silicone of the structure

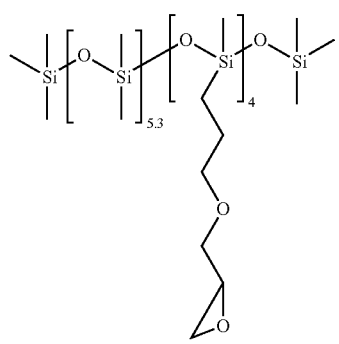

were mixed at room temperature and heated to reflux for 8 hrs. The conversion on epoxy groups was 100% (1H-NMR). The intermediate was cooled down to 50° C. A mixture consisting of 33.5 g 2-propanol and 9.95 g (0.107 mol epoxy and —Cl) of epichlorhydrin was added during 10 minutes. The mixture was heated to reflux for 17 hrs.

The solvent was removed at 50° C./20 mmHg. Afterwards, the material was washed twice with 25 ml n-hexane. The solvent was removed at 50° C./20 mmHg. An orange-yellowish opaque product of the structure

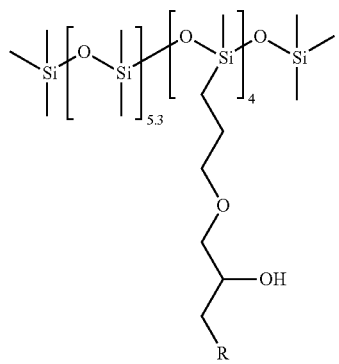

with R=

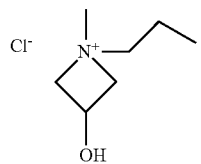

was obtained.

Example 5

Synthesis of a Quat Groups and Methylol Groups Containing Derivative 320 g 2-propanol, 47.88 g (0.256 mol —NH) ((CH$_3$)$_2$NCH$_2$CH$_2$CH$_2$)$_2$NH, and 80 g (0.255 mol epoxy groups) of an epoxy functionalized silicone of the structure

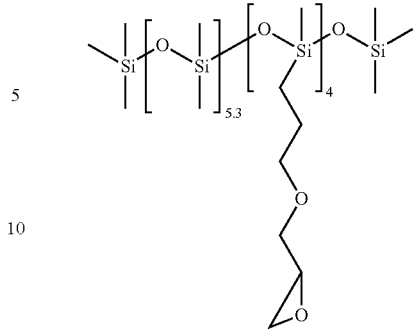

were mixed at room temperature and heated to reflux for 8 hrs. The conversion on epoxy groups was 100% (1H-NMR). The intermediate was cooled down to 75° C. A mixture consisting of 74 g 2-propanol and 47.76 g (0.511 mol —Cl) 2-chloro acetamide was added during 10 minutes. The mixture was heated to reflux for 8 hrs.

Afterwards, 289.64 g (0.260 mmol —NH$_2$) of this intermediate were placed in a separate bottle and mixed with 21.27 g (0.262 mol) of a 37% active aqueous formaldehyde solution during 30 minutes. The mixture was heated to 90° C. for 9 hrs.

The solvent was removed at 50° C./20 mmHg. Afterwards, the material was washed twice with 35 ml n-hexane. The solvent was removed at 50° C./20 mmHg. A transparent orange product of the structure

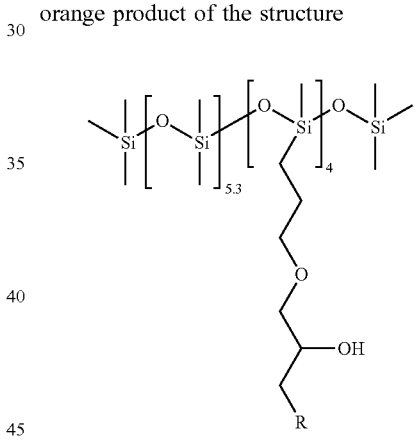

with R=

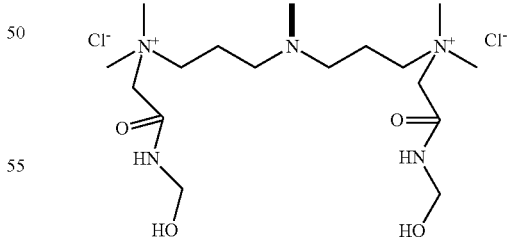

was obtained.

Example 6

Synthesis of a Methylol Derivative 400 g propylene glycol mono methyl ether, 29.9 g (0.256 mol —COOH groups) HOOCCH$_2$CH$_2$C(O)NH$_2$ (succinamic acid), 0.8 g triethylamine and 80 g (0.255 mol epoxy groups) of an epoxy functionalized silicone of the structure

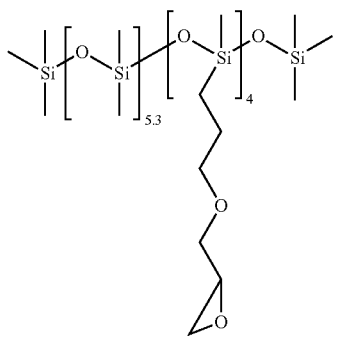

were mixed at room temperature and heated to reflux for 13 hrs. The conversion on epoxy groups was 100% (1H-NMR).

Afterwards, 255.35 g (0.127 mmol —NH$_2$) of this intermediate were placed in a separate bottle and mixed with 11.5 g (0.140 mol) of a 37% active aqueous formaldehyde solution during 30 minutes. The mixture was heated to reflux for 12 hrs.

The solvent was removed at 70° C./20 mmHg. Afterwards, the material was washed three times with 20 ml n-hexane. The solvent was removed at 70° C./20 mmHg. A transparent brownish product of the structure

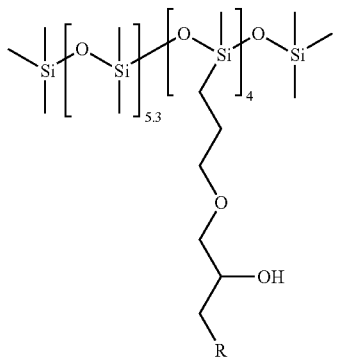

with R=

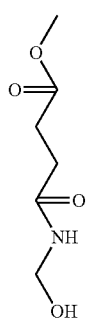

was obtained.

Example 7

Synthesis of a Thio Ester Derivative 12.62 g deionized water, 25.39 g (0.334 mol —COSH groups) thio acetic acid and 9.895 g (0.035 mol epoxy groups) of an epoxy functionalized silicone of the structure

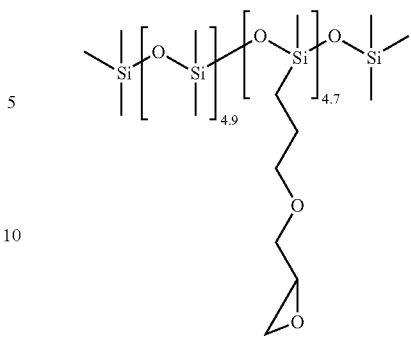

were mixed at 20° C. and maintained there for 86 hrs. The conversion on epoxy groups was 100% (1H-NMR).

The excess on thio acetic acid and water were removed at 20° C./2 mmHg. Afterwards, the residue was dissolved in 50 ml CHCl$_3$, dried over MgSO4 and subsequently filtered. The solvent was removed at 20° C./2 mmHg. A transparent slightly yellowish liquid product of the structure

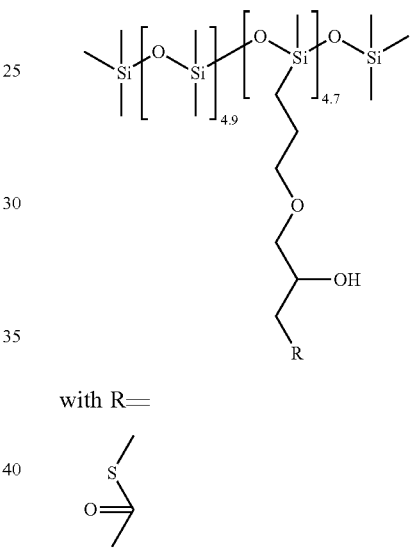

with R=

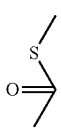

was obtained in 90% yield.

Example 8

Synthesis of a Terminal Quat Groups and Methylol Groups Containing Derivative 80 g 2-propanol, 7.72 g (0.041 mol —NH) ((CH$_3$)$_2$NCH$_2$CH$_2$CH$_2$)NH, and 20 g (0.041 mol epoxy groups) of an epoxy functionalized silicone of the structure

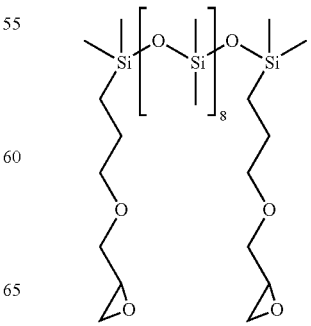

were mixed at room temperature and heated to reflux for 8 hrs. The conversion on epoxy groups was 100% (1H-NMR).

A mixture consisting of 20 g 2-propanol and 7.7 g (0.082 mol —Cl) 2-chloro acetamide was added. The mixture was heated to reflux for 8 h.

Afterwards, 6.7 g (0.082 mol) of a 37% active aqueous formaldehyde solution was added. The mixture was heated to reflux for 8 hrs.

The volatiles were removed at 70° C./20 mmHg. A transparent yellow high viscous product of the structure

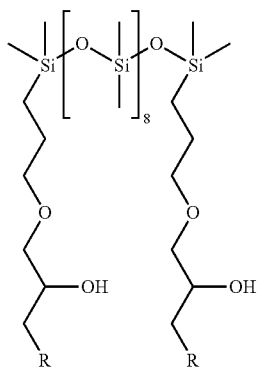

with R=

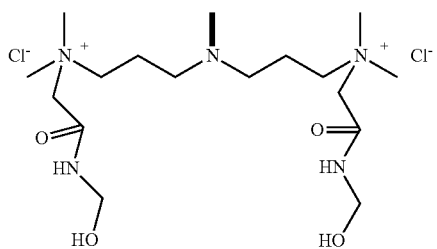

was obtained

Example 9

A set of deionized water based formulations was prepared.

All numbers are given in grams.

The data show that water based formulations can be achieved. Depending on the polymer structure type and the application purpose certain quantities on acids, bases and/or short chained alcohols are required in order to get transparent formulations.

Depending on the application purpose additional ingredients (the earlier outlined components b to j) can be added too.

Test Method for Hair Straightening

Test method for evaluation of the hair straightening is described in detail in "Chemical and Physical Behavior of human hair" Clarence R. Robbins, Springer-Verlag, New York, 1994 or in W. Cannell and L. E. Carothers, J. Soc. Cosmet. Chem. (1978) Vol. 29, pages 685-701.

The method comprises the steps to cut e.g. the hair strands into two halves, testing the control end and the corresponding treated ends of hairs on a tensile tester. FIG. 1 is showing an example of the different regions in a stress-strain curve of hairs. The resulting stress-strain curves show a region having a Hookean like behavior between A to B, whereby the yield process continues up to 30% elongation (strain). The Post Yield Slope (PYS) is related to a rapidly increase of the stress in the region between C to D. In the article of Cannell above e.g. this PYS is described in detail. The curve 1 represents an untreated hair, curve 2 represents a hair which is waved without any post-treatment. The graph shows that the post yield slope decreases after the waving treatment, indicating hair damage. The value of the post-yield slope of the treated ends of the hair is subtracted from the PYS-value of the control group. The difference expressed as percentage of the control value is a measure for the change of disulphide bonding situation after treatment. The higher the post yield slope after treatment, the least the hair damage is. The post-yield slope is directly related to the disulphide bonding in the hair fibre.

The related formula of post yield slope (PYS) is:

$$PYS = H*g*L/A \ [kg/(m \cdot s^2)]$$

H=gradient of post-yield region (kg/m)
g=9.8 m/s$^2$
L=length of fiber (m)
A=fiber cross-sectional area (m$^2$)

Example 10 Application on Latin Curly Hair

The following treatment solution (TS1) was prepared:
Polymer from example 2 (5 wt. %), 2-propanol (76 wt. %), De-ionized (DI) water (19%) The pH 8 buffer solution was composed of 100 g of 0.1 mol/L KH$_2$PO$_4$, 93.4 g of 0.1 mol/L NaOH and 6.6 g DI water.

| Formulation | F1 | F2 | F3 | F4 | F5 | F6 | F7 | F8 |
|---|---|---|---|---|---|---|---|---|
| Example | 1 | 2 | 3 | 4 | 5 | 6 | 7 | 8 |
| Silicone polymers of the examples 1 to 8 | 0.5 | 0.5 | 0.5 | 0.5 | 0.5 | 0.5 | 0.5 | 5 |
| De-ionized water | 9.0 | 9.0 | 9.0 | 9.0 | 9.5 | 6.2 | 6.2 | 5 |
| NH$_3$ in water (25%) | 0.5 | 0.5 | | | | | | |
| Acetic acid | | | 0.5 | 0.5 | | | | |
| 2-propanol | | | | | | 3.3 | 3.3 | |
| Appearance | transparent brownish | transparent brownish | transparent to slightly opaque yellowish | transparent to slightly opaque orange | transparent yellowish | transparent brownish | transparent yellowish | transparent yellowish |

Pre-Treatment

A bundle of 2 g of a Latin curly hair tress (Hair International Importers) was treated with a sodium hydroxide based commercial relaxer for 20 min to get relaxed, according to the protocol prescribed by the product manufacturer. The hair was rinsed, washed with the neutralizing shampoo sold with the commercial relaxing kit, and blow-dried in order to provide straightened relaxed hair.

Post-Treatment According to the Invention

The prepared dry hair tress was immersed in 20 ml of the treatment solution TS1 for 30 min at room temperature (25° C.). After removal of the excess liquid, the tress was immersed in 20 ml of a 0.65 wt. % aqueous solution of $FeCl_3$ for 30 min at 25° C. Afterwards, the hair was immersed in 20 ml of aqueous buffer of pH 8 defined above for 30 min. The hair was blow-dried at high dial.

50 fibers were taken randomly from the control tress and 50 fibers from the treated tress treated as described before.

The control tress was the tress treated with the relaxer pretreatment, but not treated with solution TS1.

Each of the 50 fibers were subjected to a continuous strain on a Diastron automated tensile tester. The stress or tensile strength of said single fibers were recorded as function of the strain (elongation) of the fiber.

The average values of the post yield slope and strength at 50% relative humidity (RH) at 25° C. were calculated.

It was found that the post yield slope value was increased by 14% for the 50 fibers after pre-treatment and post treatment with the TS1 solution compared to the control group only subjected to pre-treatment. The increase is significant for a p-value of <0.05 (confidence level of 95%) according to a Student t-test. The hair fibers after the post treatment of the invention was were straighter and less frizzy and provided a strength 8% higher than the control of the initial hair.

Example 11 Application on Single Bleached Hair

Pre-Treatment

A bundle of 2 g single bleached hair tress (bleached by Hair International Importers) was immersed in the treatment solution TS1 as described in example 10 for 30 min at room temperature (25° C.). After removal of the excess liquid, the tress was immersed in a 0.65 wt. % aqueous solution of $FeCl_3$ for 30 min. The hair was immersed in the aqueous buffer solution of pH 8 buffer for 30 min. The hair was then rinsed and blow-dried (hair drier or 50° C. in air). 50 fibers were taken randomly from the control tress and 50 fibers from the treated tress treated as described before.

It was found that the post yield slope value was increased by 19% for the 50 fibers after pre-treatment and post treatment with the TS1 solution compared to the control group of the original bleached hair.

The increase is significant for a p-value of <0.05 (confidence level of 95%) according to a Student t-test.

Example 12 Application on Ironed Latin Hair

Pre-Treatment

A bundle of 2 g Latin curly hair tress (Hair International Importers) was steamed with a handheld clothing steamer for 30 second, ironed for 3 passes with a flat iron at 230° C., steamed again for 30 s and ironed for another 3 passes in order to provide straightened relaxed hair.

Post-Treatment According to the Invention

The ironed dry hair tress was immersed in 20 ml of the treatment solution TS1 as described in example 10 at room temperature (25° C.) for 30 min. After removal of the excess liquid, the tress was immersed in 20 ml of a 0.65 wt. % aqueous solution of $FeCl_3$ for 30 min. The hair was immersed in 20 ml of the aqueous buffer solution of pH 8 buffer solution for 30 min. The hair was then rinsed and dried as in example 10.

The measurement of PYSd versus the control group was carried out as described in example 10.

It was found that the post yield slope value was increased by 26% for the 50 fibers after pretreatment and post treatment with the TS1 solution compared to the control group only submitted to pre-treatment. The increase is significant for a p-value of <0.05 (confidence level of 95%) according to a Student t-test. The hair fibers were straighter and less frizzy after the post treatment of the invention.

Example 13 Application Before Ironing on Latin Hair

The following treatment solution (TS2) was prepared as follows:

Polymer from example 8 (6 wt. %), in 2-propanol (75 wt. %), and De-ionized (DI) water (19%), %); the aqueous buffer solution of pH 8 buffer solution was prepared as defined above in example 10.

Treatment According to the Invention

A bundle of 2 g Latin curly hair tress (Hair International Importers) was immersed in 50 ml of the treatment solution TS2 for 1 hour at room temperature (25° C.). The excess liquid was removed by squeezing the tress between the fingers. The tress was ironed damp with a flat iron at 210° C. for 5 passes. The hair was immersed for 2 min in the aqueous buffer solution of pH 8 buffer solution and damped ironing again for 5 passes. After 2 days storage at room temperature, the hair was washed with a 10% SLES (Sodium Lauryl Ether Sulfate) solution. After immersion for 2 min in the aqueous buffer solution of pH 8 buffer, the hair was damp ironed for a third cycle at 210° C. for 5 passes.

The control tress was immersed in a diluted aminosilicone emulsion containing of 0.3% aminosilicone from the emulsion Silsoft AX-E from Momentivee in the aqueous buffer solution of pH 8 buffer solution and ironed three cycles with the same procedure as the tress treated with the solution TS2.

The hair was left 24 h at rest, washed with a 10% SLES (Sodium Lauryl Ether Sulfate) solution and blow-dried before the measurement.

It was found that the post yield slope value was increased by 18% for the 50 fibers after treatment with the TS2 solution compared to the control group subjected to treatment with aminosiloxane and ironed. The increase is significant for a p-value of <0.05 (confidence level of 95%) according to a Student t-test. The hair fibers were straighter and less frizzy after the post treatment of the invention.

Test Method for Color Retention

The test method for evaluation of the color retention is described in detail in US 2011/0219552 A1. The method determines the change in hair color (Delta E) before and after washing the hair. The color changes were determined by measuring the Hunter L, a and b values on a HunterLab colorimeter before and after washing the color treated hair tress.

The meaning of L, a, b was elaborated in "Practical Modern Hair Science" Trefor Evans and R. Randall Wichett, Alluredbooks, Carol Stream, Ill., 2012. The L value measures the lightness from L=0 (black) to L=100 (white). The color is measured by a from negative value (green) to positive value (red) and b from negative value (blue) to positive value (yellow). For example, a medium blonde has an L, a, b value of L=49, a=12, b=26 and a medium auburn has an L, a, b value of L=26, a=13, b=12.

Delta E was calculated using the following equation to evaluate color change before and after washes.

$$\text{Delta } E_w = ((L_t - L_0)^2 + (a_t - a_0)^2 + (b_t - b_0)^2)^{1/2}$$

Where $L_0$, $a_0$, $b_0$, (initial color parameters) and $L_t$, $a_t$, $b_t$ (color parameters after washing) are measured Hunter L, a, b color parameters. The larger value of Delta E the greater change of color, so smaller Delta E is desired because it indicates less color loss after washing.

Similarly, color enhancement was calculated using the following equation to evaluate initial color depth increase with treatment.

$$\text{Delta } E_e = ((L_2 - L_1)^2 + (a_2 - a_4)^2 + (b_2 - b_1)^2)^{1/2}$$

Where $L_2$, $a_2$, $b_2$, (color parameters for treated colored hair) and $L_1$, $a_1$, $b_1$ (color parameters for untreated colored hair) are measured without washing. Here a larger Delta E is desired because it means more initial color enhancement.

Example 14 Color Retention of Platinum Bleached Hair

The following treatment solution TS3 was prepared:
The treatment solution TS3 was composed of 0.6 g of polymer from example 8 and 99.3 ml of 2-Propanol. The pH 10 solution prepared by mixing 0.04 g of a 10 wt. % NaOH solution and 1000 ml of deionized water. The hair dye used was a commercial hair dye Feria 66 very rich auburn from L'Oreal.

Pre-Treatment According to Invention

A bundle of 4 g platinum bleached hair tress (International Hair Importers) was immersed in 25 ml of the pH 10 alkaline solution for 30 minutes. Then 25 ml of the treatment solution TS3 was added and the hair was kept immersed for another 30 minutes. After that, the hair was dried at room temperature overnight. The hair bundle was then washed 3 times with a 10% SLES (Sodium Lauryl Ether Sulfate) solution. The hair was dried and dyed with Feria 66 dye following the standard dyeing procedure of Feria 66.

The control tress was the tress immersed in pH10 water, but not treated by the treatment solution TS3, and washed with 10% SLES and dyed with Feria 66 dye. The initial color was measured.

Wash Protocol

The Dyed tresses were immersed in 450 ml of a 2.5% SLES solution at 41° C. The solution with the tress was stirred with a magnetic stirrer for 5 minutes at 400 rpm. After 5 minutes, the hair was dried and the hair color measured.

|  | Initial | | | After Wash | | | Color Loss Delta |
|---|---|---|---|---|---|---|---|
|  | $L_t$ | $a_t$ | $b_t$ | $L_0$ | $A_0$ | $B_0$ | $E_w$ |
| Example TS3 Treated Tress | 19.27 | 11.71 | 4.33 | 27.99 | 11.7 | 8.45 | 9.64 |
| Control Untreated Tress | 25.35 | 16.85 | 9.03 | 36.38 | 12.14 | 11.53 | 12.25 |

The color loss, Delta $E_w$ 9.64, for hair tress treated with the polymer from Example 8 was significantly less than the color loss Delta $E_w$ 12.25 for untreated hair tress control. The hair tress treated with the polymer from Example 8 displayed better color retention than the untreated tress.

Application Example 15 Color Enhancement Delta $E_e$

The following treatment solution TS3 was prepared:
The treatment solution TS3 was composed of 0.6 g of polymer from example 8 and 99.3 ml of 2-Propanol. The pH 10 solution prepared by mixing 0.04 g of a 10 wt. % NaOH solution and 1000 ml of dionized water. The hair dye used was a commercial hair dye Feria 66 very rich auburn from L'Oreal.

Pre-Treatment According to Invention

A bundle of 4 g platinum bleached hair tress (International Hair Importers) was immersed in 25 ml of the pH 10 alkaline solution for 30 minutes. Then 25 ml of the treatment solution TS3 was added and the hair was kept immersed for another 30 minutes. The hair was allowed to dry overnight at room temperature. The hair bundle was then washed 3 times with a 10% SLES (Sodium Lauryl Ether Sulfate) solution. The hair was dried and dyed with Feria 66 dye following the standard dyeing procedure of Feria 66. Once dry the color of the tress was measured.

The control tress was immersed in pH10 water, but not exposed to the treatment solution TS3. The control tress was washed with 10% sodium lauryl sulfate and dyed with Feria 66 dye. Once dried the color of the hair tress was measured.

|  | Treated Trees | | | Control untreated tress | | | Color Enhancement |
|---|---|---|---|---|---|---|---|
|  | $L_2$ | $a_2$ | $b_2$ | $L_1$ | $a_1$ | $b_1$ | Delta $E_e$ |
| Example TS3 treated tress | 19.27 | 11.71 | 4.33 | 25.32 | 16.85 | 9.03 | 9.25 |

The initial color difference between polymer from Example 8 treated hair and control is Delta $E_e$ 9.25. The polymer from Example 8 treatment enhanced the initial color.

The invention is further defined by the following non-limiting items.

Item 1: Polyorganosiloxane having an average number of 2 to 1000 siloxy units selected from the siloxy groups of the formulas:

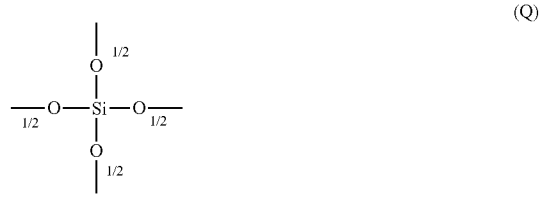

(Q)

(T)

(D)

-continued

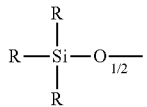
(M)

or silanes of the formula (I)

SiR$_4$ (I)

or silanes of the formula (II)

R$_3$Si—R$^3$—SiR$_3$ (II)

wherein
R is selected from R$^1$ and R$^F$, wherein
R$^1$ is selected from organic groups,
R$^F$ is selected from R$^{F1}$ and R$^{F2}$, wherein
R$^{F1}$ is selected from organic groups different from R$^1$ which contain at least one functional group F1 selected from an optionally substituted azetidine or azetidinium group and a methylol group,
R$^{F2}$ is selected from organic groups different from R$^1$ which contain at least one functional group F2 selected from:
alkoxy silyl group,
amino group,
ammonium group,
phosphine group,
phosphonium group,
epoxy group,
carbonate group,
urethane group,
isocyanate group, including blocked isocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
a mono-, di-, trihydroxy-substituted aromatic group,
mercapto group,
saccharide group,
polyether group with up to 60 carbon atoms,
thio ester and
thio ether group, and
R$^3$ is selected from divalent hydrocarbons radical which have up to 30 carbon atoms, and may contain optionally one or more groups selected from —O—, —NH—, —C(O)—, —C(S)—, tertiary amino groups

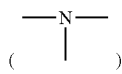

and quaternary ammonium groups

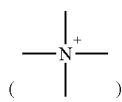

and wherein R$^3$ may optionally be substituted by one or more hydroxyl groups, with the proviso that R$^3$ is bound to the silicon atoms by a carbon atom,
with the proviso that R comprises at least one group R$^{F1}$.

Item 2: Polyorganosiloxanes according to item 1, wherein the average number of siloxy units is 2 to 300.

Item 3: Polyorganosiloxanes according to items 1 or 2, wherein R$^1$ is selected from the group consisting of n-, iso-, or tert.-C$_1$-C$_{22}$-alkyl, n-, iso-, or tert.-C$_1$-C$_{22}$-alkoxy, C$_2$-C$_{22}$-alkoxyalkyl, C$_5$-C$_{30}$-cycloalkyl, C$_6$-C$_{30}$-aryl, C$_6$-C$_{30}$-aryl(C$_1$-C$_6$)alkyl, C$_6$-C$_{30}$-alkylaryl, C$_2$-C$_{22}$-alkenyl, C$_2$-C$_{22}$-alkenyloxyalkyl, which can be each substituted by hydroxyl and halogen, and which can contain one or more ether groups.

Item 4: Polyorganosiloxanes according to any of items 1 to 3, wherein R$^{F2}$ is selected from hydrocarbon radicals which have up to 100 carbon atoms and may contain one or more groups selected from —O—, —S—, —NR$^2$—, in which R$^2$ is hydrogen, a monovalent, straight-chain, cyclic or branched, saturated, unsaturated or aromatic hydrocarbon radical which has up to 60 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —NR$^2$— groups is present, they may be the same or different, and wherein R$^{F2}$ contains at least one functional group F2.

Item 5: Polyorganosiloxanes according to any of items 1 to 4, wherein R$^{F1}$ is selected from hydroxy-substituted azetidine and azetidinium groups.

Item 6: Polyorganosiloxanes according to any of items 1 to 5, wherein R$^{F1}$ is selected from azetidine and azetidinium groups of the following formulas:

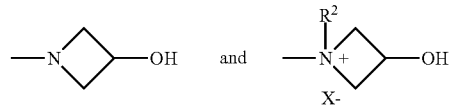

wherein R$^2$ is as defined above, and
X$^-$ is halogenide, and which azetidine or azetidinium groups are bound via a group R$^3$ to the silicon atom, wherein R$^3$ is as defined above.

Item 7: Polyorganosiloxanes according to any of items 1 to 6, wherein R$^{F1}$ is selected from methylol group-comprising moieties of the formulas:

—R$^3$—O—CH$_2$OH,

—R$^3$—N(R$^2$)(CH$_2$OH),

—R$^3$—N$^+$(R$^2$)$_2$(CH$_2$OH),

—R$^3$—N(CH$_2$OH)$_2$

—R$^3$—N$^+$(R$^2$)(CH$_2$OH)$_2$

—R$^3$—C(O)—NH—CH$_2$OH

—R$^3$—C(O)—N(CH$_2$OH)$_2$ wherein R$^3$ and R$^2$ are as defined above.

Item 8: Polyorganosiloxanes according to item 7, wherein R³ comprises a moiety of the formula:

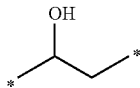

(wherein each * denote a bond).

Item 9: Polyorganosiloxanes according to item 8, wherein the moiety of the formula:

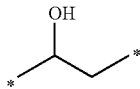

(wherein each * denote a bond), is formed by the ring opening reaction of an epoxide or carbonate group.

Item 10: Polyorganosiloxanes according to item 9, wherein the epoxide or carbonate groups are selected from:

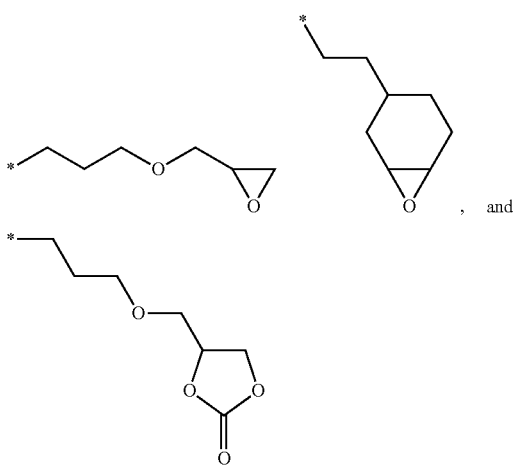

(wherein each * denote a bond), which groups are bound to the silicon atom of a siloxy group from the left side.

Item 11: Polyorganosiloxanes according to any of items 1 to 10, which contain at least one siloxy group of the formula $M^F$:

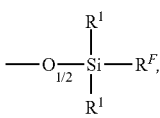

wherein $R^1$ and $R^F$ are as defined above.

Item 12: Polyorganosiloxanes according to any of items 1 to 10, selected from the formulas:

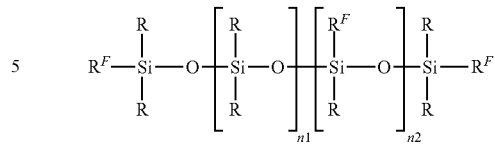

wherein

R is $R^1$, and $R^F$ is as defined above, with the proviso that at least one $R^F$ is $R^{F1}$, and the sum of the average numbers n1+n2 is 0 to 28,

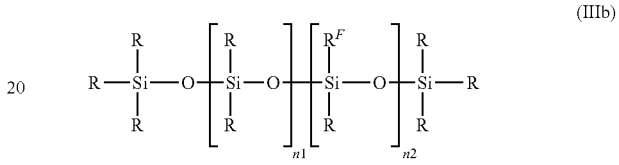

wherein

R is $R^1$, and $R^F$ is as defined above, with the proviso that at least one $R^F$ is $R^{F1}$, and the sum of the average numbers n1+n2 is 1 to 28, with n2≥1,

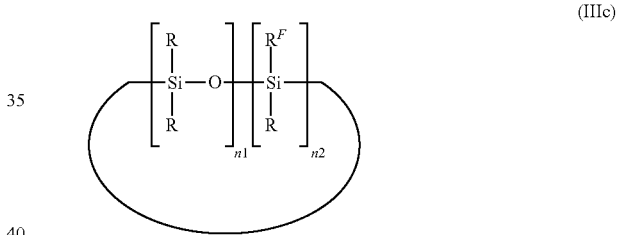

R is $R^1$, and $R^F$ is as defined above, with the proviso that at least one $R^F$ is $R^{F1}$, and wherein the sum of the average numbers n1+n2 is 3 to 7 with n2≥1.

Item 13: A method for treating amino acid based substrates comprising the step of applying to such amino acid based substrate at least one polyorganosiloxane having an average number of 2 to 1000 siloxy units selected from the siloxy groups of the formulas:

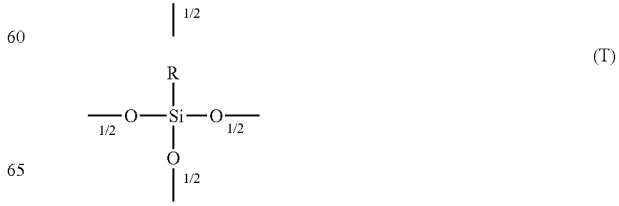

-continued

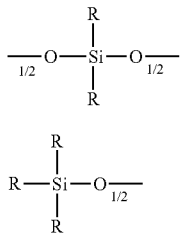
(D)

(M)

or at least one silane of the formula (I')

$$SiR_4 \quad (I')$$

or at least one silane of the formula (II')

$$R_3Si-R^3-SiR_3 \quad (II')$$

wherein

R is selected from $R^1$ and $R^{F3}$, wherein $R^1$ is selected from organic groups, $R^{F3}$ is selected from $R^{F4}$ and $R^{F5}$, wherein $R^{F4}$ is selected from organic groups different from $R^1$ which contain at least one functional group F4 selected from an optionally substituted azetidine or azetidinium group,
a methylol group,
a mono-, di-, trihydroxy-substituted aromatic group,
a thio ester and
a thio ether group, $R^{F5}$ is selected from organic groups different from $R^1$ which contain at least one functional group F5 selected from:

alkoxy silyl group,
amino group,
ammonium group,
phosphonium group,
epoxy group,
carbonate group,
urethane group,
isocyanate group, including blocked isocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
mercapto group,
saccharide group, and
polyether group with up to 60 carbon atoms,
and $R^3$ is selected from divalent hydrocarbons radical which have up to 30 carbon atoms, and may contain optionally one or more groups selected from —O—, —NH—, —C(O)—, —C(S)—, tertiary amino groups

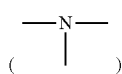

and quaternary ammonium groups

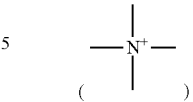

and wherein $R^3$ may optionally be substituted by one or more hydroxyl groups, with the proviso that $R^3$ is bound to the silicon atoms by a carbon atom, with the proviso that R comprises at least one group $R^{F4}$.

Item 14: A method for treating amino acid based substrates according to item 13, wherein the polyorganosiloxanes have an average number of siloxy units of from 2 to 300.

Item 15: A method for treating amino acid based substrates according to items 13 or 14, wherein in the polyorganosiloxanes $R^1$ is selected from the group consisting of n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_2$-alkenyl, $C_2$-$C_{22}$-alkenyloxyalkyl, which can be each substituted by hydroxyl and halogen, and which can contain one or more ether groups.

Item 16: A method for treating amino acid based substrates according to items to any of items 13 to 15, wherein in the polyorganosiloxanes $R^{F5}$ is selected from hydrocarbon radicals which have up to 100 carbon atoms and may contain one or more groups selected from —O—, —S—, —$NR^2$—, in which $R^2$ is hydrogen, a monovalent, straight-chain, cyclic or branched, saturated, unsaturated or aromatic hydrocarbon radical which has up to 60 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —$NR^2$— groups is present, they may be the same or different, and wherein $R^{F5}$ contains at least one functional group F5.

Item 17: A method for treating amino acid based substrates according to items to any of items 13 to 16, wherein in the polyorganosiloxanes $R^{F4}$ is selected from hydroxy-substituted azetidine and azetidinium groups.

Item 18: A method for treating amino acid based substrates according to items to any of items 13 to 17, wherein in the polyorganosiloxanes $R^{F4}$ is selected from azetidine and azetidinium groups of the following formulas:

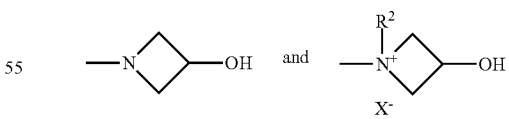

wherein $R^2$ is as defined above, and $X^-$ is halogenide, and which azetidine or azetidinium groups are bound via a group $R^3$ to the silicon atom, wherein $R^3$ is as defined above.

Item 19: A method for treating amino acid based substrates according to items to any of items 13 to 16, wherein in the polyorganosiloxanes $R^{F4}$ is selected from methylol group-comprising moieties of the formulas:

$$—R^3—O—CH_2OH,$$

—R³—N(R²)(CH₂OH),

—R³—N⁺(R²)₂(CH₂OH),

—R³—N(CH₂OH)₂

—R³—N⁺(R²)(CH₂OH)₂

—R³—C(O)—NH—CH₂OH

—R³—C(O)—N(CH₂OH)₂ wherein R³ is defined above.

Item 20: A method for treating amino acid based substrates according to item 19, wherein in the polyorganosiloxanes R³ comprises a moiety of the formula:

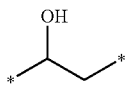

(wherein each * denote a bond).

Item 21: A method for treating amino acid based substrates according to item 20, wherein in the polyorganosiloxanes the moiety of the formula:

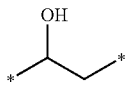

is formed by the ring opening reaction of an epoxide or carbonate group.

Item 22: A method for treating amino acid based substrates according to item 21, wherein the epoxide or carbonate groups are selected from:

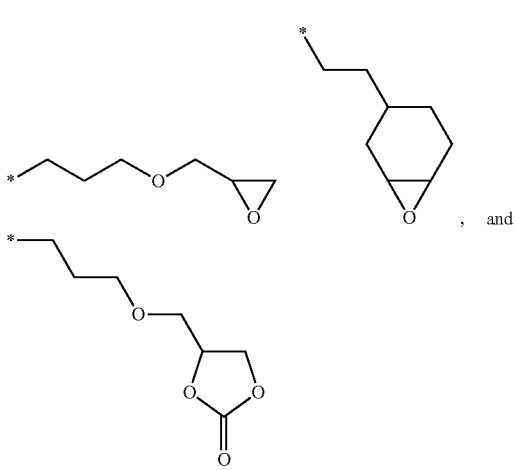

(wherein each * denote a bond), which groups are bound to the silicon atom of a siloxy group from the left side.

Item 23: A method for treating amino acid based substrates according to any of items 13 to 22, wherein the polyorganosiloxanes contain at least one siloxy group of the formula M^F:

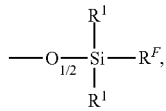

wherein R¹ is as defined above, and R^F is R^{F3} as defined above.

Item 24: A method for treating amino acid based substrates according to any of items 13 to 23, wherein the polyorganosiloxanes are selected from the formulas:

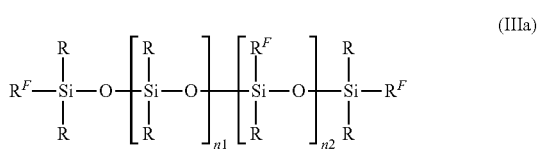
(IIIa)

wherein
R is R¹, and R^F is as defined above, with the proviso that at least one R^F is R^{F1}, and the sum of the average numbers n1+n2 is 0 to 28,

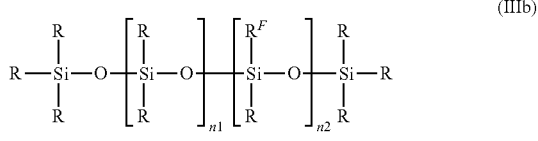
(IIIb)

wherein
R is R¹, and R^F is as defined above, with the proviso that at least one R^F is R^{F1}, and the sum of the average numbers n1+n2 is 1 to 28; with 2≥1,

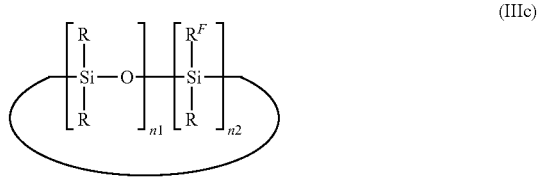
(IIIc)

R is R¹, and R^F is as defined above, with the proviso that at least one R^F is R^{F1}, and wherein the sum of the average numbers n1+n2 is 3 to 7 with n2≥1.

Item 25: A method for treating amino acid based substrates according to any of items 13 to 24, wherein the amino acid based substrates is hair.

Item 26: A method according to item 25, comprising the steps of
a) pretreatment of the hair with a reducing formulation comprising substances which break and transform —S—S-disulfide bridges into —SH thiol structures,
b) application of the polysiloxanes or silanes as defined in any of the items 13 to 24 or compositions comprising the same to the hair,
c) shaping of the hair,
d) post treatment of the hair after shaping with an oxidizing formulation comprising substances which accelerate the transformation of —SH thiol structures into —S—S-disulfide bridges, e) optional post treatment of the hair after shaping with a complexing formulation,
f) optional application of hair dyeing components.

Item 27: A method according to item 25, comprising the steps of
a) hot ironing of the hair,
b) application of the polysiloxanes or silanes as defined in any of the items 13 to 24 or compositions comprising the same to the hair,
c) optional post treatment of the hair after shaping with a complexing formulation,
d) optional application of hair dyeing components.

Item 28: A method according to item 25, comprising the steps of
a) application of the polysiloxanes or silanes as defined in any of the items 13 to 24 or compositions comprising the same to the hair,
b) hot ironing of the hair,
c) optional post treatment of the hair after shaping with a complexing formulation,
d) optional application of hair dyeing components.

Item 29: A method according to item 25, comprising the steps of
a) optionally pretreatment of the hair with an aqueous alkaline solution,
b) application of the polysiloxanes or silanes as defined in any of the items 13 to 24 or compositions comprising the same to the hair, and
c) application of hair dyeing components to the hair.

Item 30: Use of a polyorganosiloxane having an average number of 2 to 1000 siloxy units selected from the siloxy groups of the formulas:

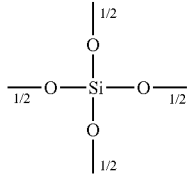  (Q)

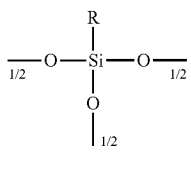  (T)

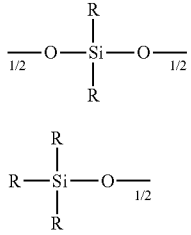  (D)

  (M)

or at least one silane of the formula (I')

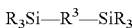  (I')

or at least one silane of the formula (II')

$R_3Si-R^3-SiR_3$  (II')

wherein
R is selected from $R^1$ and $R^{F3}$, wherein
$R^1$ is selected from organic groups,
$R^{F3}$ is selected from $R^{F4}$ and $R^{F5}$, wherein
$R^{F4}$ is selected from organic groups different from $R^1$ which contain at least one functional group F4 selected from an optionally substituted azetidine or azetidinium group,
a methylol group,
a mono-, di-, trihydroxy-substituted aromatic group,
a thio ester and
a thio ether group,
$R^{F5}$ is selected from organic groups different from $R^1$ which contain at least one functional group F5 selected from:
alkoxy silyl group,
amino group,
ammonium group,
phosphonium group,
epoxy group,
carbonate group,
urethane group,
isocyanate group, including blocked isocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
mercapto group,
saccharide group, and
polyether group with up to 60 carbon atoms,
and
$R^3$ is selected from divalent hydrocarbons radical which have up to 30 carbon atoms, and may contain optionally one or more groups selected from —O—, —NH—, —C(O)—, —C(S)—, tertiary amino groups

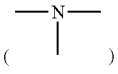

and quaternary ammonium groups

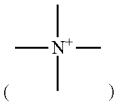

and wherein $R^3$ may optionally be substituted by one or more hydroxyl groups, with the proviso that $R^3$ is bound to the silicon atoms by a carbon atom,
with the proviso that R comprises at least one group $R^{F4}$, for the treatment of amino acid based substrates.

Item 31: Use according to item 30, wherein the amino acid based substrates are selected from keratinous substrates.

Item 32: Use according to items 30 and 31, wherein the keratinous substrate is selected from human hair.

Item 33: Use according to any of items 30 to 32, in hair treatments, selected from hair straightening treatment, hair conditioning treatment, hair shine treatment, hair UV protecting treatment, hair washing treatment, hair coloring treatment, permanent shaping treatment of hairs, protecting dyed hair color treatment, e.g. after hair wash, hair color retention treatment, hair color enhancement treatment, and/or reduced color fading treatment of artificially colored hair.

Item 34: A composition for treating amino acid based substrates, comprising
a) at least one polyorganosiloxane as defined in any of items 13 to 24 or at least one silane of the formula (I') or (II') as defined in item 13,
b) at least one diluent/solvent
c) optionally one or more protein, preferably keratin,
d) optionally one or more surface active ingredient/emulsifier,
e) optionally one or more emollient/fatty substance,
f) optionally one or more preservative,
g) optionally one or more skin protecting ingredient,
h) optionally one or more conditioning agent,
i) optionally one or more oxidizing agent,
j) optionally one or more reducing agent,
k) optionally one or more other auxiliary,
with the proviso that oxidizing agents and reducing agents are not present simultaneously in a given formulation.

Item 35: A composition for treating amino acid based substrates according to item 34, comprising the components in the following weight portions:

| | Ingredient | weight % |
|---|---|---|
| a) | silicone actives according to component a) | 0.05 to 30 |
| b) | diluents/solvents | 5 to 99.95 |
| c) | protein, preferred keratin | 0 to 15 |
| d) | surface active ingredients/emulsifiers | 0 to 15 |
| e) | emollients/fatty substance | 0 to 15 |
| f) | Preservatives | 0 to 5 |
| g) | skin protecting ingredients | 0 to 10 |
| h) | conditioning agents | 0 to 90 |
| i) | oxidizing agents agents | 0 to 10 |
| j) | reducing agents | 0 to 10 |
| k) | other auxiliary agents | 0 to 10 |

Item 36: A composition for treating amino acid based substrates according to items 34 or 35, comprising an additional polyorganosiloxane compound different from component a).

Item 37: A method for treating amino acid based substrates comprising the step of applying at least one composition according to any of items 34 to 36 to such amino acid based substrate.

Item 38: A kit including at least two containers wherein at least one container comprises a composition according to any of the items 34 to 36, and wherein at least one other container comprises an aqueous solution of a metal salt.

The invention claimed is:

1. A method for treating amino acid based substrates comprising the step of applying to such amino acid based substrate at least one polyorganosiloxane having an average number of 2 to 1000 siloxy units selected from the siloxy groups of the formulas:

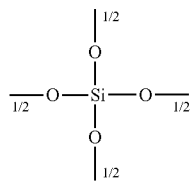
(Q)

-continued

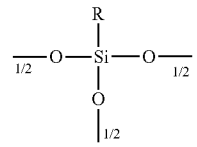
(T)

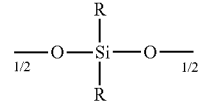
(D)

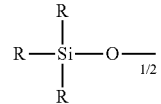
(M)

or at least one silane of the formula (I')

$$SiR_4 \quad (I')$$

or at least one silane of the formula (II')

$$R_3Si—R^3—SiR_3 \quad (II')$$

wherein
R is selected from $R^1$ and $R^{F3}$, wherein
$R^1$ is selected from organic groups,
$R^{F3}$ is selected from $R^{F4}$ and $R^{F5}$, wherein
$R^{F4}$ is selected from organic groups different from $R^1$ which contain at least one functional group F4 selected from
a mono-, di-, trihydroxy-substituted aromatic group,
$R^{F5}$ is selected from organic groups different from $R^1$ which contain at least one functional group F5 selected from:
an optionally substituted azetidine or azetidinium group,
a methylol group,
a thio ester,
a thio ether group,
alkoxy silyl group,
amino group,
ammonium group,
phosphonium group,
epoxy group,
carbonate group,
urethane group,
isocyanate group, including blocked iscocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
mercapto group,
saccharide group, and
polyether group with up to 60 carbon atoms,
and
$R^3$ is selected from divalent hydrocarbons radical which have up to 30 carbon atoms, and may contain optionally one or more groups selected from —O—, —NH—, —C(O)—, —C(S)—, tertiary amino groups

and quaternary ammonium groups

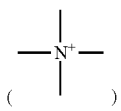

and wherein $R^3$ may optionally be substituted by one or more hydroxyl groups, with the proviso that $R^3$ is bound to the silicon atoms by a carbon atom, with the proviso that R comprises at least one group $R^{F4}$.

2. The method according to claim 1, wherein the polyorganosiloxanes have an average number of siloxy units of from 2 to 300.

3. The method according to claim 1, wherein in the polyorganosiloxanes $R^1$ are selected from the group consisting of n-, iso-, or tert.-$C_1$-$C_{22}$-alkyl, $C_2$-$C_{22}$-alkoxyalkyl, $C_5$-$C_{30}$-cycloalkyl, $C_6$-$C_{30}$-aryl, $C_6$-$C_{30}$-aryl($C_1$-$C_6$)alkyl, $C_6$-$C_{30}$-alkylaryl, $C_2$-$C_{22}$-alkenyl, $C_2$-$C_{22}$-alkenyloxyalkyl, which can be each substituted by hydroxyl and halogen, and which can contain one or more ether groups.

4. The method according to claim 1, wherein in the polyorganosiloxanes $R^{F5}$ are selected from hydrocarbon radicals which have up to 100 carbon atoms and may contain one or more groups selected from —O—, —S—, —$NR^2$—, in which $R^2$ is hydrogen, a monovalent, straight-chain, cyclic or branched, saturated, unsaturated or aromatic hydrocarbon radical which has up to 60 carbon atoms and may contain one or more groups selected from —O—, —NH—, —C(O)— and —C(S)—, and which may optionally be substituted by one or more substituents selected from the group consisting of a hydroxyl group, an optionally substituted heterocyclic group preferably containing one or more nitrogen atoms, amino, alkylamino, dialkylamino, polyether radicals and polyetherester radicals, where, when a plurality of —$NR^2$— groups is present, they may be the same or different, and wherein $R^{F5}$ contains at least one functional group F5.

5. The method according to claim 1, wherein in the polyorganosiloxanes $R^{F5}$ are selected from hydroxy-substituted azetidine and azetidinium groups.

6. The method according to claim 1, wherein in the polyorganosiloxanes $R^{F5}$ is selected from azetidine and azetidinium groups of the following formulas:

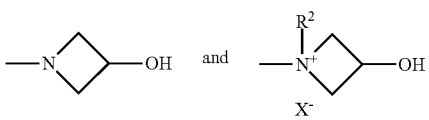

wherein $R^2$ is as defined above, and $X^-$ is halogenide, and which azetidine or azetidinium groups are bound via a group $R^3$ to the silicon atom, wherein $R^3$ is as defined above.

7. The method according to claim 1, wherein in the polyorganosiloxanes $R^{F5}$ is selected from methylol group-comprising moieties of the formulas:

—$R^3$—O—$CH_2OH$,

—$R^3$—$N(R^2)(CH_2OH)$,

—$R^3$—$N^+(R^2)_2(CH_2OH)$,

—$R^3$—$N(CH_2OH)_2$

—$R^3$—$N^+(R^2)(CH_2OH)_2$

—$R^3$—C(O)—NH—$CH_2OH$

—$R^3$—C(O)—$N(CH_2OH)_2$ wherein $R^3$ is defined above.

8. A method for treating amino acid based substrates according to claim 6, wherein in the polyorganosiloxanes $R^3$ comprises a moiety of the formula:

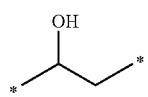

is formed by the ring opening reaction of an epoxide or carbonate group selected from:

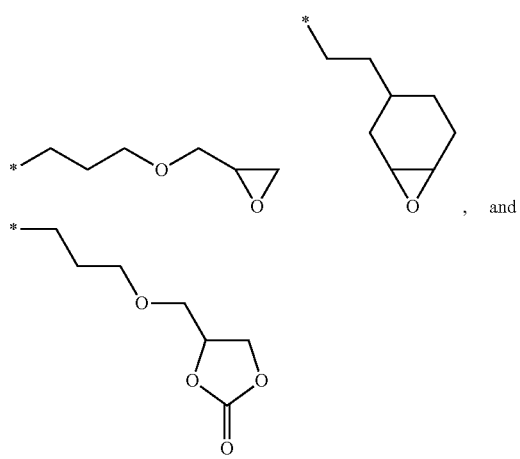

wherein each * denote a bond,
which groups are bound to the silicon atom of a siloxy group from the left side.

9. The method of claim 1, wherein the polyorganosiloxanes contain at least one siloxy group of the formula $M^F$:

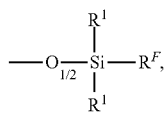

wherein $R^1$ is as defined above, and $R^F$ is $R^{F3}$ as defined above.

10. The method of claim 1, wherein the polyorganosiloxanes are selected from the formulas:

(IIIa)

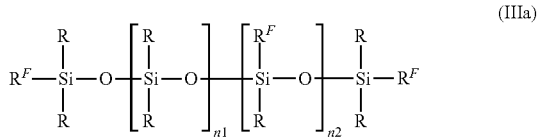

wherein
R is R¹, and $R^F$ is as defined above, with the proviso that at least one $R^F$ is $R^{F1}$, and the sum of the average numbers n1+n2 is 0 to 28,

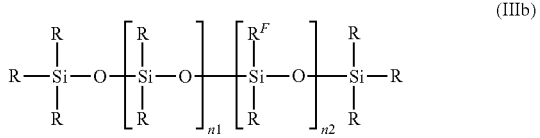
(IIIb)

wherein
R is R¹, and $R^F$ is as defined above, with the proviso that at least one $R^F$ is $R^{F1}$, and the sum of the average numbers n1+n2 is 1 to 28, with n2≥1, and

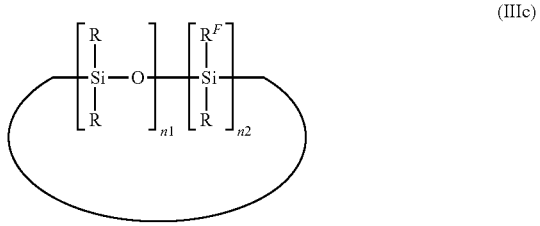
(IIIc)

R is R¹, and $R^F$ is as defined above, with the proviso that at least one $R^F$ is $R^{F1}$, and wherein the sum of the average numbers n1+n2 is 3 to 7 with n2≥1.

11. The method of claim 1, wherein the amino acid based substrates are selected from keratinous substrates.

12. The method of claim 1, wherein the amino acid based substrate is hair.

13. The method of claim 2, wherein the hair is selected from human hair.

14. A method according to claim 12, comprising the steps of:
a) pretreatment of the hair with a reducing formulation comprising substances which break and transform —S—S-disulfide bridges into —SH thiol structures,
b) application of the polysiloxanes or silanes as defined in any of the claim 1 or compositions comprising the same to the hair,
c) shaping of the hair,
d) post treatment of the hair after shaping with an oxidizing formulation comprising substances which accelerate the transformation of —SH thiol structures into —S—S-disulfide bridges,
e) optional post treatment of the hair after shaping with a complexing formulation,
f) optional application of hair dyeing components.

15. A method according to claim 12, comprising the steps of:
a) hot ironing of the hair,
b) application of the polysiloxanes or silanes as defined in any of the claim 1 or compositions comprising the same to the hair,
c) optional post treatment of the hair after shaping with a complexing formulation,
d) optional application of hair dyeing components.

16. A method according to claim 12, comprising the steps of:
a) application of the polysiloxanes or silanes as defined in any of the claim 1 or compositions comprising the same to the hair:
b) hot ironing of the hair,
c) optional post treatment of the hair after shaping with a complexing formulation,
d) optional application of hair dyeing components.

17. A method according to claim 12, comprising the steps of:
a) optionally pretreatment of the hair with an aqueous alkaline solution,
b) application of the polysiloxanes or silanes as defined in any of the claim 1 or compositions comprising the same to the hair, and,
c) application of hair dyeing components to the hair.

18. A method for treating amino acid based substrates according to claim 12, which method is a hair treatment, selected from hair straightening treatment, hair conditioning treatment, hair shine treatment, hair UV protecting treatment, hair washing treatment, hair coloring treatment, permanent shaping treatment of hairs, protecting dyed hair color treatment, e.g. after hair wash, hair color retention treatment, hair color enhancement treatment, and/or reduced color fading treatment of artificially colored hair.

19. A method for treating amino acid based substrates according to claim 1, comprising the step of applying to such amino acid based substrate a composition comprising:
a) at least one polyorganosiloxane as defined in any of claim 1 or at least one silane of the formula (I') or (II') as defined in claim 1
b) at least one diluent/solvent,
c) optionally one or more protein, preferably keratin,
d) optionally one or more surface active ingredient/emulsifier,
e) optionally one or more emollient/fatty substance,
f) optionally one or more preservative,
g) optionally one or more skin protecting ingredient,
h) optionally one or more conditioning agent,
i) optionally one or more oxidizing agent,
j) optionally one or more reducing agent,
k) optionally one or more other auxiliary,
with the proviso that oxidizing agents and reducing agents are not present simultaneously in a given formulation.

20. A method for treating amino acid based substrates according to claim 19, comprising the components in the following weight portions

|   | Ingredient | weight % |
| --- | --- | --- |
| a) | silicone actives according to component a) | 0.05 to 30 |
| b) | diluents/solvents | 5 to 99.95 |
| c) | protein, preferred keratin | 0 to 15 |
| d) | surface active ingredients/emulsifiers | 0 to 15 |
| e) | emollients/fatty substance | 0 to 15 |
| f) | Preservatives | 0 to 5 |
| g) | skin protecting ingredients | 0 to 10 |
| h) | conditioning agents | 0 to 90 |
| i) | oxidizing agents agents | 0 to 10 |
| j) | reducing agents | 0 to 10 |
| k) | other auxiliary agents | 0 to 10. |

21. A method for treating amino acid based substrates according to claim 19, comprising an additional polyorganosiloxane compound different from component a).

22. A kit including at least two containers wherein at least one container comprises a composition according to any of the claim 19, and wherein at least one other container comprises an aqueous solution of a metal salt.

23. The method according to claim 1, wherein $R^{F5}$ is selected from organic groups different from R¹ which contain at least one functional group F5 selected from:

alkoxy silyl group,
amino group,
ammonium group,
phosphonium group,
epoxy group,
carbonate group,
urethane group,
isocyanate group, including blocked iscocyanate group,
urea group,
amido group,
aldehyde group,
acetale or half acetale group,
Schiff-Base or enamine group,
zwitterionic group,
carboxylic acid or carboxylate group,
sulfonic acid or sulfonate group,
sulfuric acid half ester or sulfate group,
phosphoric acid ester or phosphate group,
phosphonic acid ester or phosphonate group,
phosphorous acid ester or phosphite group,
xanthogenate/xanthogenate ester group,
thiosulfato group,
mercapto group,
saccharide group, and
polyether group with up to 60 carbon atoms.

* * * * *